US007815623B2

(12) United States Patent
Bankiewicz et al.

(10) Patent No.: US 7,815,623 B2
(45) Date of Patent: Oct. 19, 2010

(54) STEPPED CANNULA

(75) Inventors: Krzysztof Bankiewicz, Oakland, CA (US); Jürg M. Sommer, Orinda, CA (US)

(73) Assignees: Genzyme Corporation, Framingham, MA (US); The Regents of the University of California, Oakland, CA (US)

( * ) Notice: Subject to any disclaimer, the term of this patent is extended or adjusted under 35 U.S.C. 154(b) by 750 days.

(21) Appl. No.: 11/243,756

(22) Filed: Oct. 5, 2005

(65) Prior Publication Data

US 2006/0135945 A1 Jun. 22, 2006

Related U.S. Application Data

(60) Provisional application No. 60/641,551, filed on Jan. 4, 2005, provisional application No. 60/616,238, filed on Oct. 5, 2004.

(51) Int. Cl.
*A61M 25/00* (2006.01)
(52) U.S. Cl. ..................................... 604/506
(58) Field of Classification Search ............... 604/506, 604/164.1, 164.11, 264
See application file for complete search history.

(56) References Cited

U.S. PATENT DOCUMENTS

| 4,149,535 | A | | 4/1979 | Volder |
| 4,239,042 | A | | 12/1980 | Asai |
| 4,448,532 | A | | 5/1984 | Storz et al. |
| 4,449,532 | A | * | 5/1984 | Storz ..................... 606/191 |
| 4,543,092 | A | | 9/1985 | Mehler et al. |
| 4,597,421 | A | | 7/1986 | Wells |
| 4,629,450 | A | | 12/1986 | Suzuki et al. |
| 4,738,658 | A | | 4/1988 | Magro et al. |
| 4,739,768 | A | | 4/1988 | Engelson |
| 4,781,691 | A | | 11/1988 | Gross |
| 4,978,334 | A | | 12/1990 | Toye et al. |
| 5,069,673 | A | | 12/1991 | Shwab |
| 5,720,720 | A | * | 2/1998 | Laske et al. ............. 604/500 |
| 5,851,203 | A | | 12/1998 | Van Muiden |
| 5,902,282 | A | | 5/1999 | Balbierz |
| 5,919,171 | A | | 7/1999 | Kira et al. |
| 6,020,196 | A | * | 2/2000 | Hu et al. ................. 435/366 |

(Continued)

FOREIGN PATENT DOCUMENTS

GB 1255551 A 12/1971

(Continued)

OTHER PUBLICATIONS

Chen et al, Variables affecting convection-enhanced delivery to the striatum: a systematic examination of rate of infusion, cannula size, infusate concentration, and tissue-cannula sealing time, 1999 J. Neurosurgery, vol. 90 pp. 315-320.*

(Continued)

*Primary Examiner*—Nicholas D Lucchesi
*Assistant Examiner*—Aarti B Berdichevsky
(74) *Attorney, Agent, or Firm*—Robins & Pasternak LLP; Roberta L. Robins

(57) ABSTRACT

Described herein are cannulas having a stepped exterior. Also described are methods of making and using these cannulas, for example to deliver one or more materials to the central nervous system of an animal.

30 Claims, 10 Drawing Sheets

U.S. PATENT DOCUMENTS

| | | | |
|---|---|---|---|
| 6,030,369 A * | 2/2000 | Engelson et al. | 604/264 |
| 6,042,579 A * | 3/2000 | Elsberry et al. | 604/891.1 |
| 6,186,986 B1 | 2/2001 | Berg et al. | |
| RE37,410 E * | 10/2001 | Brem et al. | 424/484 |
| 6,309,634 B1 | 10/2001 | Bankiewicz et al. | |
| 6,524,299 B1 | 2/2003 | Tran et al. | |
| 6,533,751 B2 | 3/2003 | Cragg et al. | |
| 6,641,564 B1 | 11/2003 | Kraus | |
| 7,037,295 B2 | 5/2006 | Tiernan et al. | |
| 7,182,944 B2 * | 2/2007 | Bankiewicz | 424/93.2 |
| 2002/0087152 A1 * | 7/2002 | Mikus et al. | 606/21 |
| 2002/0091372 A1 | 7/2002 | Cragg et al. | |
| 2002/0095081 A1 * | 7/2002 | Vilsmeier | 600/407 |
| 2002/0114780 A1 * | 8/2002 | Bankiewicz et al. | 424/85.1 |
| 2002/0141980 A1 * | 10/2002 | Bankiewicz et al. | 424/93.21 |
| 2003/0073934 A1 * | 4/2003 | Putz | 600/585 |
| 2004/0092879 A1 | 5/2004 | Kraus et al. | |
| 2004/0209810 A1 * | 10/2004 | Gill et al. | 514/12 |
| 2004/0215162 A1 * | 10/2004 | Putz | 604/500 |
| 2005/0154297 A1 * | 7/2005 | Gill | 600/431 |
| 2005/0256503 A1 | 11/2005 | Hall | |
| 2006/0073101 A1 * | 4/2006 | Oldfield et al. | 424/9.34 |
| 2006/0129126 A1 * | 6/2006 | Kaplitt et al. | 604/513 |
| 2006/0217664 A1 * | 9/2006 | Hattler et al. | 604/164.1 |
| 2007/0088295 A1 * | 4/2007 | Bankiewicz | 604/264 |
| 2007/0110798 A1 * | 5/2007 | Drummond et al. | 424/450 |
| 2007/0250021 A1 | 10/2007 | Brimhall et al. | |
| 2007/0254842 A1 * | 11/2007 | Bankiewicz | 514/12 |
| 2008/0228168 A1 * | 9/2008 | Mittermeyer et al. | 604/525 |
| 2009/0088695 A1 * | 4/2009 | Kapur et al. | 604/164.01 |
| 2009/0088730 A1 * | 4/2009 | Hoofnagle et al. | 604/533 |
| 2009/0143764 A1 * | 6/2009 | Nelson | 604/510 |
| 2009/0198218 A1 * | 8/2009 | Gill et al. | 604/524 |

FOREIGN PATENT DOCUMENTS

| | | |
|---|---|---|
| WO | WO 02/053205 A | 7/2002 |

OTHER PUBLICATIONS

Bankiewicz et al., "Convection-enhanced delivery of AAV vector in parkinsonian monkeys; in vivo detection of gene expression and restoration of dopaminergic function using pro-drug approach," (2000) Exp. Neurol. 164(1):2-14.

Lieberman et al., "Convection-enhanced distribution of large molecules in gray matter during interstitial drug infusion," (1995) J. Neurosurg. 82(6):1021-9.

Marshall et al., "Biocompatibility of cardiovascular gene delivery catheters with adenovirus vectors: an important determinant of the efficiency of cardiovascular gene transfer," (2000) Mol. Ther. 1(5 Pt 1):423-9.

Naimark et al., "Adenovirus-catheter compatibility increases gene expression after delivery to porcine myocardium," (2003) Hum. Gene Ther. 14(2):161-6.

Quereshi et al., "Multicolumn Infusion of Gene Therapy Cells into Human Brain Tumors: Technical Report," (2000) Neurosurgery 46(3):663-9.

Tsui et al., "Stability of adenoviral vectors following catheter delivery," (2001) Mol. Ther. 3(1):122-5.

Declaration of Christian Matthias Luz, M.D. Submitted in U.S. Appl. No. 11/507,939 Signed on Aug. 21, 2009.

Information Disclosure Statement by Applicant Submitted in U.S. Appl. No. 11/507,939 Mailed on Jun. 19, 2008. Considered by the Examiner on Jun. 19, 2008, 2 Pages.

Official Action Mailed on Jun. 26, 2008 in U.S. Appl. No. 11/507,939, 12 Pages.

Amendment in Response to the Jun. 26, 2008 Office action in U.S. Appl. No. 11/507,939, Mailed Dec. 24, 2008, 14 Pages.

Information Disclosure Statement by Applicant Submitted in U.S. Appl. No. 11/507,939 Mailed on Mar. 18, 2009, Considered by the Examiner on Mar. 19, 2009, 6 Pages.

Official Action Mailed on Mar. 23, 2009 in U.S. Appl. No. 11/507,939, 16 Pages.

Amendment in Response to the Mar. 23, 2009 Office Action in U.S. Appl. No. 11/507,939, Mailed Aug. 24, 2009, 15 Pages.

Information Disclosure Statement by Applicant Submitted in U.S. Appl. No. 11/507,939, Received by the USPTO on Oct. 27, 2009, Considered by the Examiner on Dec. 4, 2009, 3 Pages.

Official Action Mailed on Dec. 7, 2009 on U.S. Appl. No. 11/507,939, 18 pges.

Yin, et al., "Optimal Region of the Putamen for Image-Guided Convection-Enhanced Delivery of Therapeutics in Human and Non-Human Primates," *NeuroImage* Epublication, pp. 1-8 (2009).

* cited by examiner

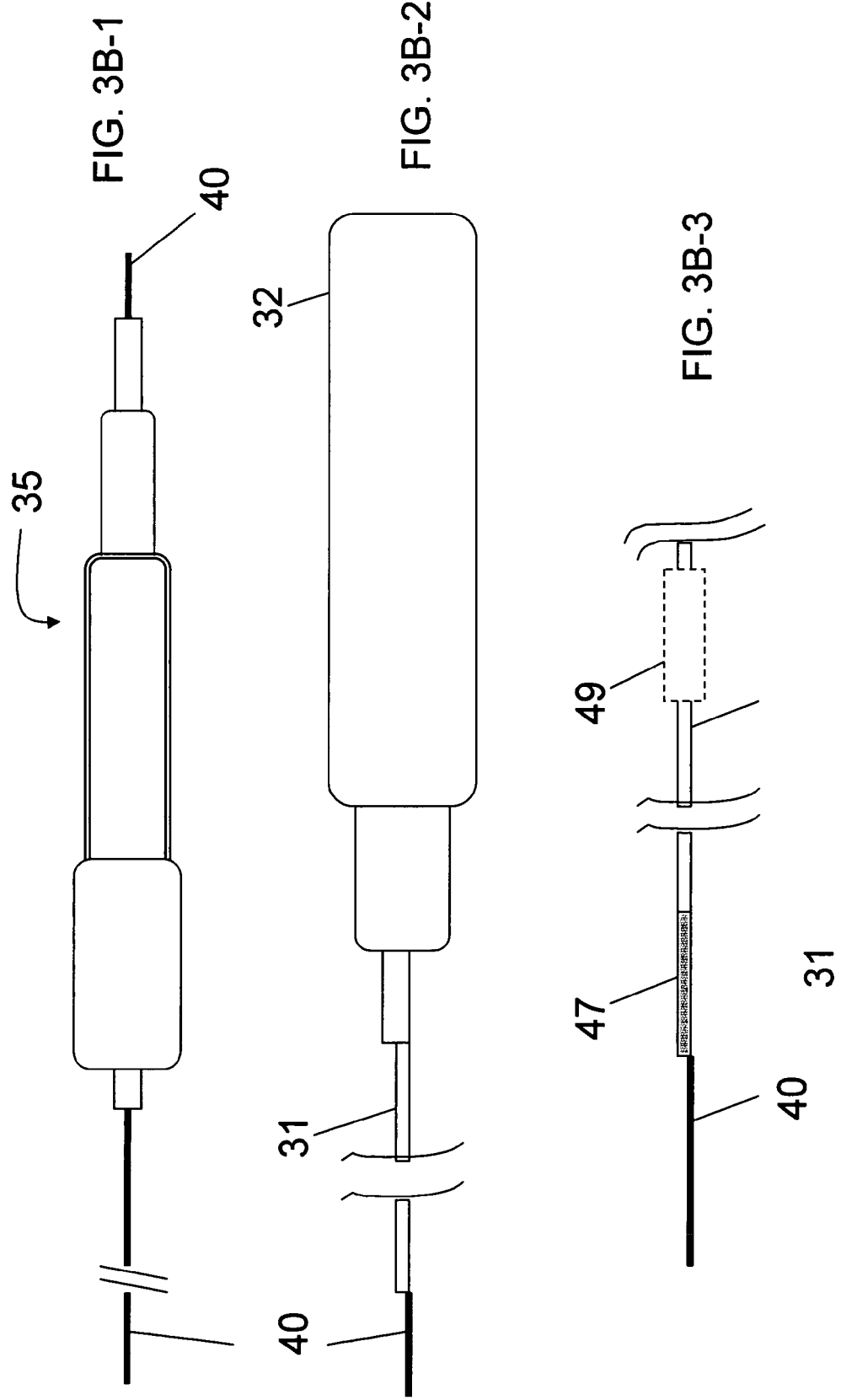

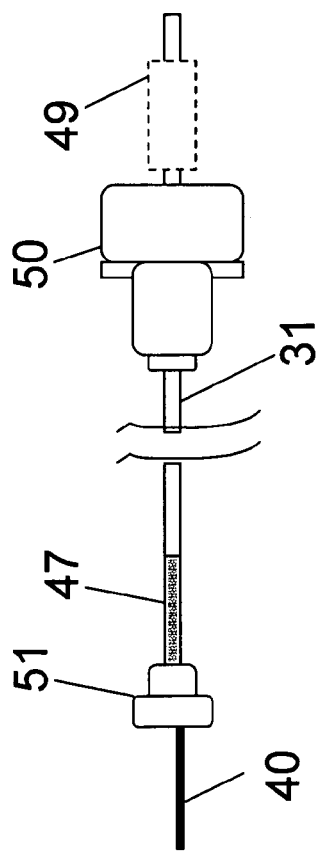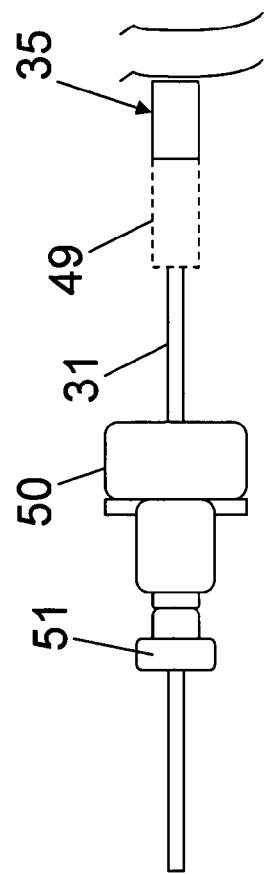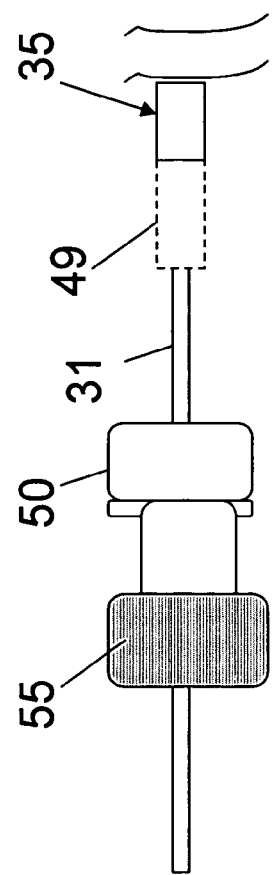

US 7,815,623 B2

STEPPED CANNULA

CROSS-REFERENCE TO RELATED APPLICATIONS

This application claims the benefit of U.S. provisional application 60/616,238, filed Oct. 5, 2004 and 60/641,551, filed Jan. 4, 2005, both of which applications are incorporated by reference herein in their entireties.

TECHNICAL FIELD

This invention is in the field of cannulas. In particular, the invention relates to cannulas for delivering a material, for example a biologically active agent, into the central nervous system, to systems comprising these cannulas as well as to methods of making and using these cannulas.

BACKGROUND

Cannulas can be used to deliver materials into the central nervous system (CNS) of a subject. However, with current cannula designs, care must be taken to prevent reflux of the material along the injection track. Quereshi et al. (2000) Neurosurgery 46(3): 663-69. Even with precautions are taken to minimize reflux, such as slow removal of the cannula and the application of pressure to the tissue as the cannula is removed, reflux remains a problem.

In addition, a substantial portion of the material being delivered can be lost due to exposure of the material to the large surface area of the inside of the cannula. In particular, exposure to stainless steel can cause substantial loss of the material to be delivered. For example, various groups have demonstrated that a substantial amount of adenovirus vectors preparations exposed to stainless steel surfaces are lost. Naimark et al. (2003) *Hum. Gene Ther.* 14:161-6; Tsui et al. (2001) *Mol. Ther.* 3:122-5; Marshall et al. (2000) *Mol. Ther.* 1(5 Pt 1):423-9. The problem is exacerbated when very small volumes of material are being delivered, because the smaller the volume, the greater the ratio of surface area to volume within the cannula. Given that the use of small volumes of material is particularly desirable in situations where the material is expensive or difficult to obtain, it would be desirable to have devices and methods in which both reflux and loss of material are minimized.

Thus, there exists a need for a cannula capable of introducing materials into the brain of a subject without reflux of the material along the needle track. A need also exists for cannula designs that reduce the loss of agents to the inner surface(s), and, accordingly, can deliver small volumes of material effectively.

SUMMARY

The present invention solves these and other problems by providing cannula designs that reduce or eliminate reflux and/or loss of the delivered material.

In one aspect, the present invention relates to cannulas for the delivery of agents to a target tissue in an animal. In some embodiments the target tissue is the central nervous system (e.g., brain). In some embodiments the agent is a biologically active agent.

In one embodiment, the cannula comprises an external step design in which the diameter of the cannula in contact with the material to be delivered decreases in a stepwise fashion at defined points along its length. Thus, in one aspect, the invention includes a stepped cannula having an exterior diameter, a distal end, a proximal end and a lumen extending between the proximal and distal ends, the stepped cannula comprising two or more co-axially disposed segments, each segment having an exterior diameter that defines the exterior diameter of the cannula, wherein the exterior diameter of the segments is different.

In certain embodiments, the exterior diameter has the step configuration while the interior surface in contact with the material does not have the step configuration.

In any of the embodiments described herein, the decrease in diameter may be in a proximal to distal direction (i.e., the step at the proximal end of the cannula having the largest diameter and the step at the distal end having the smallest diameter). There may be any number of steps along the exterior diameter, for example, 1, 2, 3, 4, 5, 6, 7, 8, 9, 10 or even more.

In any of the embodiments described herein, the diameter of the steps may increase by the same amount from step to step (i.e., the difference in diameter between adjacent steps is uniform). Alternatively, in any of the embodiments described herein, the difference in diameter of the steps may vary from step to step along the length of the cannula. In addition, in any of the embodiments described herein, the distance between steps may be the same or it may vary. In one embodiment, the cannula has the structure and dimensions as described below in Example 1 and in reference to FIGS. 3A and/or 3B.

The cannulas described herein may be made of any material, including metals, metal alloys, polymers or combinations thereof. In certain embodiments, the cannula comprises stainless steel exterior with a non-stainless steel surface that contacts the product to be delivered. For example, the surface of the lumen of the cannula (which is contact with the material to be delivered) may be comprised of a polymeric coating over the stainless steel. Alternatively, the cannula may further comprise one or more tubes extending through the lumen of the cannula, for example fused silica tubing encased in the stainless steel outer sleeve of the cannula, such that in use product contacts the inner surface of the fused silica tubing rather than stainless steel. As noted above, the surface in contact with the material to be delivered may or may not have a step configuration. In yet another embodiment, the cannula is constructed as shown in FIGS. 3A and 3B from the materials discussed below.

In any of the cannulas described herein, the cannula may comprise two or more materials. In certain embodiments, a stainless steel cannula surrounds a fused silica tubing, in which the surface contacted by the material to be delivered is quartz silica. In other embodiments, a stainless steel exterior surrounds a fused silica inner surface, in which the surface contacted by the material to be delivered is fused silica. In a preferred embodiment the cannula has the structure, dimensions and is made of the materials as described in Example 1 and shown in FIGS. 3A and 3B.

In another aspect, the invention includes a cannula assembly comprising: any of the cannulas described herein and a reservoir comprising the one or more materials to be delivered through the cannula, the reservoir operably connected to the lumen of the cannula. The one or more materials (e.g., potentially therapeutic formulations), are also referred to herein as "product(s)". In certain embodiments, the reservoir comprises a syringe. Further, in any of the systems or assemblies described herein, the cannula and/or reservoir can be operably linked to one or more pumps (e.g., syringe pumps). In certain embodiments, the cannulas are operably linked to the pump(s) via tubing that extends through the lumen of the cannula. In certain embodiments, the systems described herein further comprise a stereotactic frame (see, e.g., FIG. 5).

The materials delivered by these systems may comprise one or more biologically active agents (e.g., AAV vectors, proteins, drugs, etc.), dyes, tracers, markers, contrast agents or combinations thereof. Furthermore, the systems may be used for delivery to any part of the body, most preferably to the brain of an animal. In one embodiment, the invention provides a cannula that has a decreased hold-up volume.

In another aspect, the invention includes a method of delivering one or more materials to a target area in a subject, the method comprising the steps of positioning a cannula or cannula assembly as described herein at the target area of the subject; and delivering the one or more materials to the target area through the cannula. In certain embodiments, the target area is in the central nervous system, for example, the brain.

These and other embodiments of the subject invention will readily occur to those of ordinary skill in the art in view of the disclosure herein.

BRIEF DESCRIPTION OF THE DRAWINGS

FIG. 3B-1 through 3B-6, are side views depicting various steps involved in the assembly of an exemplary injection needle assembly (INA) as described herein.

FIG. 4 depicts an overview of an exemplary Medfusion 2010i syringe pump with an attached syringe.

FIG. 5 is an overview of an exemplary cannula as described herein attached to a stereotactic frame for administration of product to a human subject.

FIG. 6 is an overview of another exemplary cannula as described herein.

DETAILED DESCRIPTION

The present invention relates to novel cannulas for delivery of materials (e.g. formulations comprising potentially therapeutic agents) to a target tissue of an animal, such as the brain. The cannulas described herein greatly reduce or eliminate reflux during delivery of the materials. Such materials are referred to herein generally as "product." More specifically, the present invention enables delivery of product to well-defined locations within the brain of a subject with minimal reflux of product along the needle track, with minimal hold-up volume, and with minimal losses of product to the internal surfaces of the cannula.

In one embodiment of the present invention, the cannula has a step design in which the diameter of the cannula decreases in a stepwise fashion at defined points along its length (from proximal to distal region). Thus, in preferred embodiments, the smallest cannula diameter is at the distal most portion of the cannula. As noted above, this step design reduces reflux of product along the needle track. In one embodiment the exterior surface of the cannula comprises five segments differing in external diameter, forming four steps, and in another embodiment it has the structure and dimensions discussed below. The surface of the cannula may be smooth, as in the embodiment illustrated in FIGS. 3A and 3B.

Figure 1:
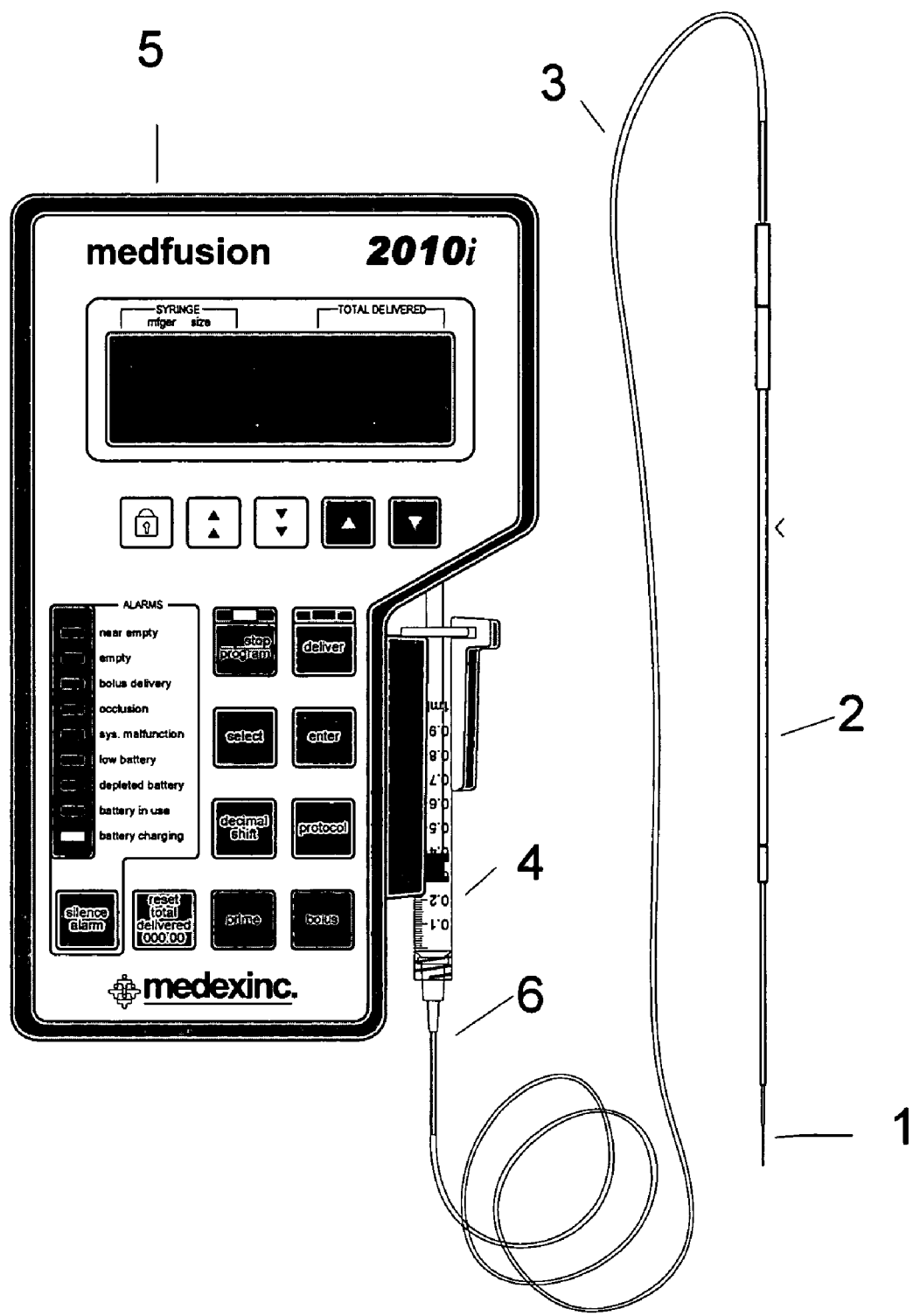
FIG. 1 is an overview of an exemplary system comprising a stepped cannula 2 as described herein. Also shown is a syringe 4, which is linked to the cannula 2 via fused silica tubing 1, 3 inside FEP Class VI tubing 3, and a syringe pump 5. Syringe pump 5 is connected to tubing 3 via Luer compression fitting 6.

FIG. 1 shows an overview of an exemplary system comprising a stepped cannula 2 with a stainless steel exterior. Fused silica tubing 1, 3 extends through the lumen of cannula 2 and links cannula 2 to syringe 4 via hub and/or blunt needle 6 on the syringe 4. Syringe 4 is also attached to computerized syringe pump 5. The cannula includes a means for reducing or eliminating reflux of the material to be delivered, for example, tubing (e.g., fused silica) which extends through the lumen of the stepped cannula and is in contact the material to be delivered.

The exemplary embodiment depicted in FIG. 1 shows a cannula 2 having a total of four "steps." It will be apparent that the steps nearest the distal end of the cannula are those that enter the target tissue first, and, accordingly, the number of steps entering the target tissue (e.g. brain) will depend on the depth of penetration needed to reach that target in the subject animal. With respect to delivery to the brain, the operator can readily determine the appropriate depth of penetration, taking into account both the size of the animal being treated and the location within the brain that is being targeted.

As shown in FIG. 1 the exterior diameter of the cannula 2 decreases at each step along the length of the cannula, in a proximal to distal direction. As used herein, proximal refers to points close to the syringe 4 from which product is dispensed, and distal refers to points close to the point of ultimate product delivery (e.g. the target tissue).

FIG. 1 depicts an exemplary embodiment in which the two proximal-most segments, which border the proximal-most step, have approximately the same length, while the four distal-most segments are of varying lengths from each other and from the two proximal-most segments. Thus, it will be apparent that some, all or none of the segments between the steps may have the same length as other segments.

Non-limiting examples of materials which may be used to the various components of the cannula and/or systems comprising the cannula are shown in the following table:

| Component (in reference to FIG. 1) | Part | Source | Composition | Product Contact |
|---|---|---|---|---|
| Tubing 1 at distal end of cannula | Fused Silica Tubing at tip | Polymicro | Quartz silica and Polyimide coating | Yes; Silica portion only |
| Cannula 2 | 23G to 15G steel tubing | Ranfac | Stainless Steel | No |
| Tubing 3* connecting cannula 2 to syringe 4 | Fused Silica Tubing | Polymicro | Quartz silica and Polyimide coating | Yes; Silica portion only |
| Syringe 4 | Syringe | BD | USP Class VII Polypropylene | Yes |
| Pump 5 | Pump | Medfusion | Multiple materials | No |
| Luer joint 6 | Luer Hub/blunt needle (from 23 G × 1½ needle) | BD | (USP Class VII Polypropylene) and Stainless | Yes |
| Joints** | Glue joints | Locktight | Cyanoacrylate | Yes |

*fused silica inside FEP Class VI tubing. FEP tubing does not have product contact
**between 1 and 2; Between 2 and 3; Between 3 and 6

Figure 2:
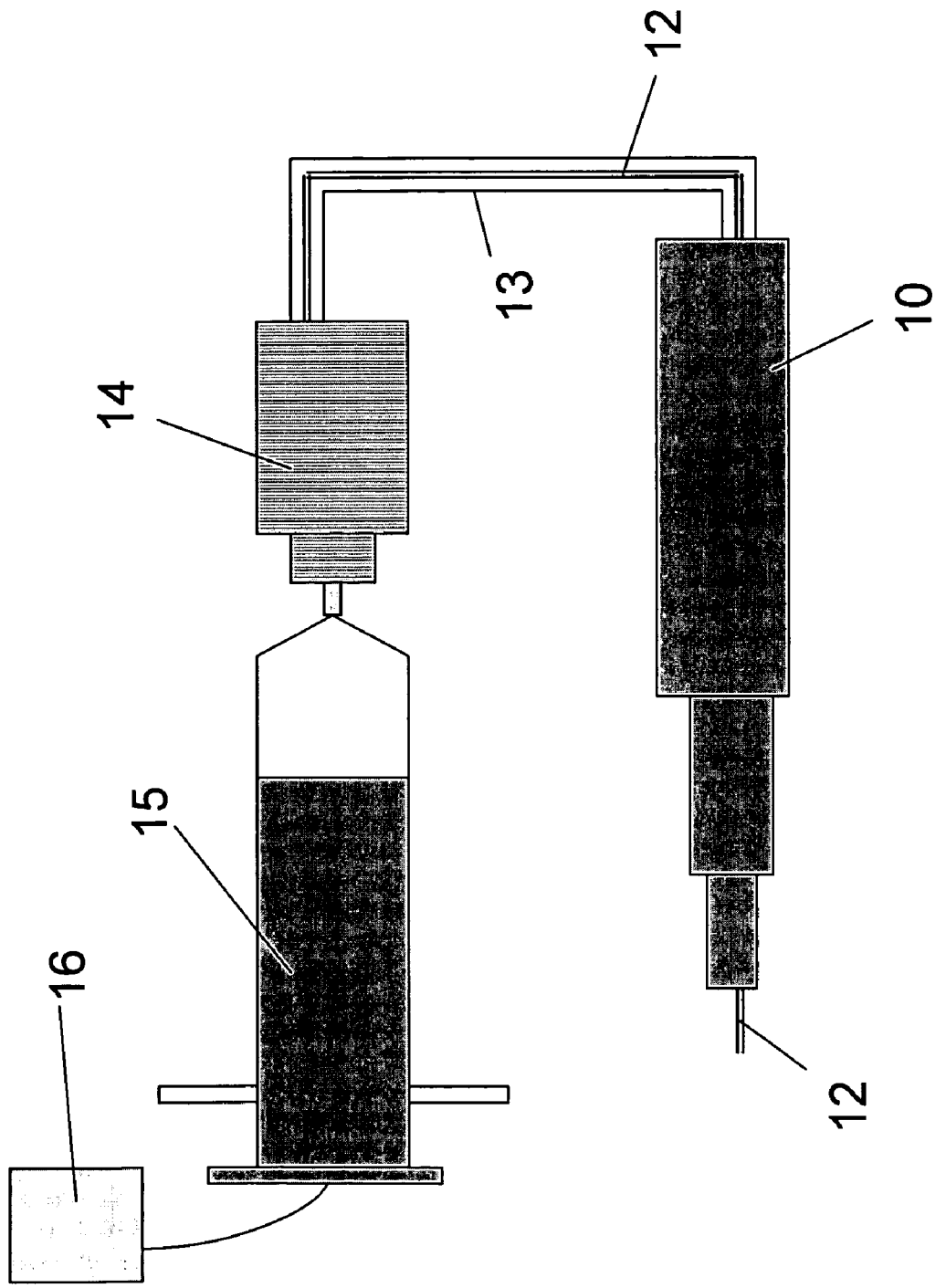
FIG. 2 is a side view of another exemplary system comprising an exemplary stepped cannula 10 as described herein. Also shown is a syringe pump 16 and a syringe 15, which is linked to the cannula 10 at a Luer compression fitting 14 via fused silica tubing 12 extending through the lumen of a FEP (Teflon) tubing 13 and the cannula 10.

FIG. 2 shows an overview of an exemplary system similar to that shown in FIG. 1. The embodiment shown in FIG. 2 comprises a stepped stainless steel cannula 10 with fused silica tubing 12 running through the lumen of the stainless steel cannula and extending beyond the distal end of the cannula 10. Also shown in FIG. 2 are tubing (FEP) 13 covering the fused silica tubing 12, as well as a Luer compression fitting 14 and 1 inch stainless steel (23 ga) between fused silica tubing 12 and FEP tubing 13. The Luer compression fitting 14 is connected to a syringe 15, which in turn is connected to a pump 16.

Exemplary materials and exemplary commercial sources of these materials that can be used in making an embodiment such as that shown in FIG. 2 are set forth in the following table:

| Component (reference # in FIG. 2) | Exemplary Commercial Source | Composition | Product Contact |
|---|---|---|---|
| Cannula 10 | Ranfac | 304 SS | No |
| Fused Silica Tubing 12 | PolymicroTechnologies | Fused silica w/polyimide coating on outside | Yes |
| Teflon Tubing 13 | Western Analytical Products | Teflon ® (FEP) | No |
| Luer fitting 14 | Upchurch Scientific | Polypropylene with ETFE | Yes |
| Syringe 15 | BD | Polypropylene | Yes |
| Pump 16 | Medfusion | N/A | No |

As shown, in certain embodiments, tubing extends through the lumen of cannula and the product(s) to be delivered are delivered through this tubing. In embodiments containing the tubing, the tubing may be flush with the distal end of the cannula. Alternatively, in preferred embodiments, the tubing extends from the distal end of the cannula. In such embodiments, the amount which the tubing extends may vary depending on the application. Generally, the tubing will extend from about 1 mm to about 1 cm from the cannula (or any length therebetween), more preferably from about 1 to about 50 mm (or any length therebetween), and even more preferably from about 1 mm to about 25 mm (or any length therebetween, including, but not limited to, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm or 25 mm). In one preferred embodiment, the tubing extends approximately 10 mm beyond the distal end thereof.

As shown in the Figures, the tubing extending through the cannula may have one more coatings or surrounding materials in one or more regions, for example to protect the tubing in contact with the produce to be delivered. Thus, in certain embodiments, tubing (e.g., FEP (Teflon) tubing) protects the portion of the fused silica tubing extending beyond the proximal end of the stainless steel cannula. The fused silica tubing may be connected to the syringe by any suitable means, including, but not limited to, a Luer compression fitting, and the syringe is driven by a syringe pump (manual, electronic and/or computerized). It will apparent that the syringe size can be selected by the operator to deliver the appropriate amount of product(s). Thus, 1 mL, 2.5 mL, 5 mL, or even larger syringes may be used.

In certain embodiments, the Luer compression fitting comprises a 1 inch stainless steel 23G spacer between the fused silica (inner) tubing and the FEP (outer) tubing. The optional spacer, provides mechanical rigidity at the Luer compression fitting and helps seal the gap between the inner and outer tubing when the ferrule is glued in place using Loctite® adhesive. This gap must be filled to prevent product from entering the space between the inner and outer tubing as it is being administered to a subject. Preferably, the proximal end of the spacer represents the only stainless steel product contact surface of the systems and cannulas described herein. This minimal stainless steel product contact surface may be eliminated if desired by applying Loctite® adhesive or other coating to cover the otherwise exposed end of the spacer, to provide a system with absolutely no stainless steel contact with product. Alternatively the spacer could be comprised of a different material.

Figure 3A:
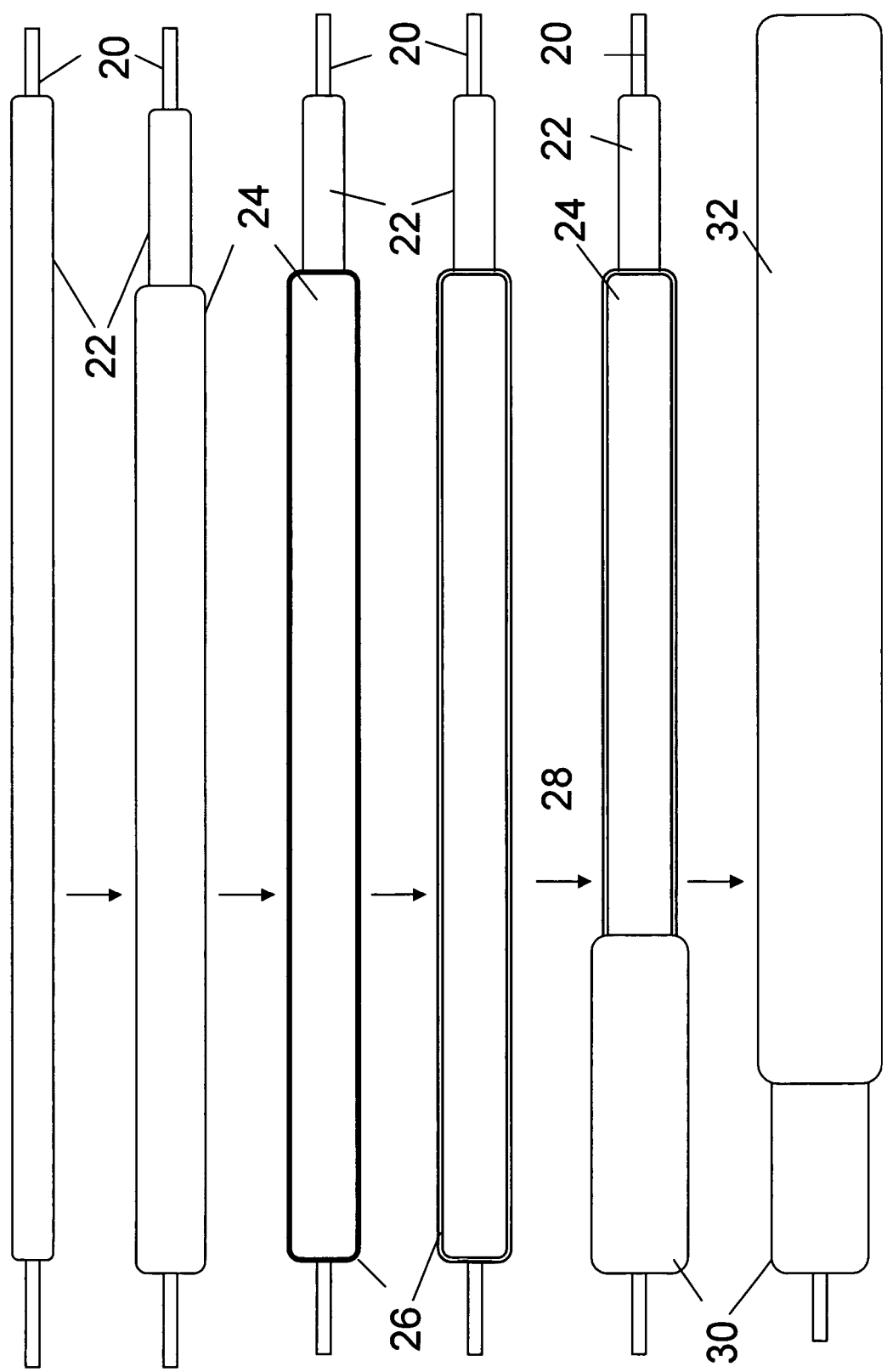
FIG. 3A depicts side views showing exemplary steps involved in the assembly of an exemplary injection needle sub-assembly (INSA) as described herein.

FIG. 3A depicts selected exemplary steps in making a stepped cannula as described herein. See, also, Example 1. In particular, the step design cannula that reduced reflux may be assembled in the order shown by the arrows (top to bottom), namely by adding components (20, 22, 24, 26, 28, 30) of increasing diameters. Thus, as described in Example 1, various length segments are joined together to form the step design.

When the cannula is made from two or more pieces, the joints should not allow materials to leak from the cannula into the target tissue or vice versa (from the target tissue into the cannula). Accordingly, the joints are preferably sealed. The joints can be sealed in a variety of ways, including but not limited to, welding (e.g., laser welding), adhesives, sealants, heating (e.g., for thermoplastic polymers) and combinations thereof. It will be apparent that the nature of the seal will depend on the material used to make the cannula, for example welding may be used for stainless steel cannulas while heating may be used for thermoplastic polymers.

A step design cannula as described herein can also be formed in a single integral piece, for example by injection molding a stepped cannula as described herein.

FIG. 3B1-6 depict assembly of an exemplary stepped cannula as described herein. As described in Example 1, the stepped cannula 35 shown in FIG. 3A is prepared by removing the needle guard 32 and inserting an inner tubing component 40 through the cannula 35 until it extends from the ends of the cannula. (FIG. 3B-1). Any material may be used for the inner tubing component 40, including but not limited to fused silica tubing.

As an alternative to tubing, it will be apparent that the inside of the steel cannula 35 can be coated with one or more materials that contact the product to be delivered, thereby reducing loss of the product to the steel cannula during delivery. Various techniques of coating of stainless steel materials are known and may be used.

Optionally, adhesive may be placed on the tubing 40 such that the tubing is secured to the needle. Any suitable adhesive can be used, for example, Loctite® adhesive. Preferably, the bond strength of the adhesive is at least about 4 lbs, more preferably at least about 5 lbs.

In the embodiment shown in FIG. 3B, the needle guard 32 may be replaced and a previously-cut length of tubing 31 (e.g., FEP tubing) extended over the fused silica tubing 40 through the cannula 35 (FIG. 3B-2). The length of the outer tubing 31 can be determined by the indication and can range from 10 inches to 5 yards in length (or any value therebetween). Thus, in certain embodiments, the outer tubing covers the full-length of the inner tubing and may extend over the inner tubing. Alternatively, in other embodiments, the outer tubing 31 does not fully extend over the length of the inner tubing 40 (FIG. 3B-2). Any suitable adhesive may be used to secure the outer tubing 31 to the assembly, for example at the ends of the outer tubing 31. The bond strength of the adhesive is preferably at least about 5 lbs.

As shown in FIG. 3B-3, one or more spacer components 47 may be inserted over the inner and/or outer tubing 40, 31. The spacer 47 may be made of any material including metals, metal alloys, polymers and combinations thereof. In certain embodiments, the spacer 47 comprises stainless steel. The spacer 47 can be any length, although it is preferably that does not extend over the needle. Optionally, a component may be included to help seal the components of the assembly, for example a length of PVC shrink tubing 49. See, Example 1 for exemplary dimensions of space and PVC tubing components.

Figure 4:
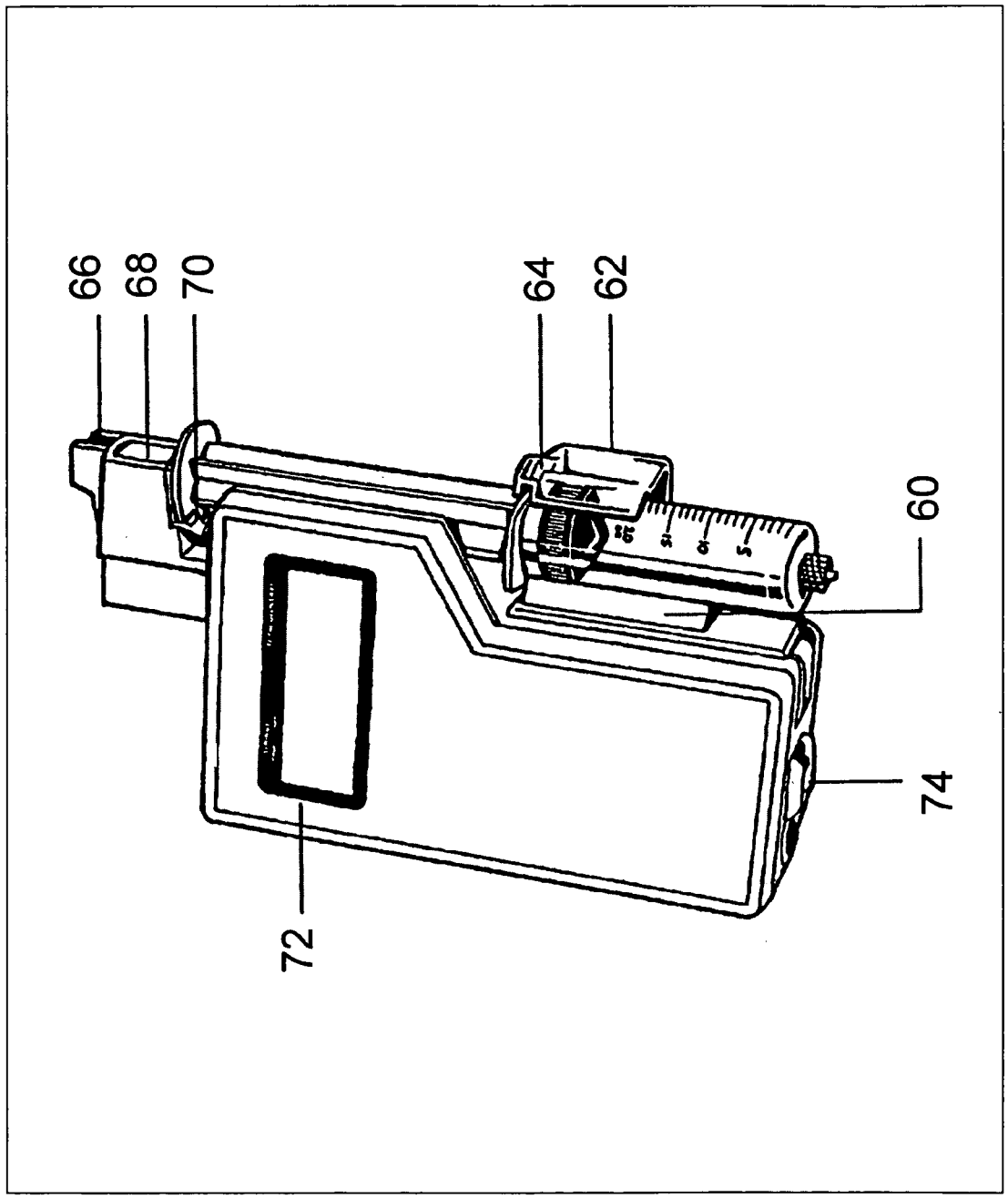

Subsequently, the assembly may be fitted with one or more components that allow it to be conveniently linked to a product delivery reservoir. For example, as shown in FIG. 3B-4, appropriately sized female Luer compression fitting 50 is slid over a length of the outer tubing 31 and a ferrule 51 is placed over the outer tubing 31, preferably such that it is flush with the end of the outer tubing 31. Adhesive may be optionally applied to one or more of the components (e.g., outside of the end of outer tubing prior to fitting of ferrule on the end and/or to seal the joints between the inner tubing, spacer, outer tubing and ferrule.

The length of inner tubing 40 extending from the ferrule 51 may be removed, for example by scoring the tubing and snapping or cutting it off and the ferrule 51 fitted inside of the Luer compression fitting 50 (FIG. 3B-5). The shrink tubing 49 may be heated to seal the joint. Finally, a male Luer compression fitting 55 can be assembled and fitting onto the female Luer compression fitting 50 and ferrule 51.

As noted above, the stepped cannulas described herein may be made out of the variety of materials that are physiologically acceptable, including but not limited to metals, metal alloys, polymers, organic fibers, inorganic fibers and/or combinations thereof. In preferred embodiments, the cannula comprises stainless steel (e.g. 316SS or 304SS).

Optionally, a product-contact surface (e.g., tubing or coating) may extend through the lumen of the cannula. A variety of materials may also be used for the optional product-contact surface, including but not limited to metals, metal alloys, polymers, organic fibers, inorganic fibers and/or combinations thereof. Preferably, the product-contact surface is not stainless steel. In such embodiments, the outer cannula must still be made of a material physiologically compatible with the target tissue, but there since there is no product contact it need not be compatible with the biologically active agent or product formulation. Similarly, in such embodiments the FEP (Teflon) tubing shown in the Figures may be replaced with other tubing without regard to whether the tubing material is compatible with the biologically active agent or product formulation.

Thus, in one embodiment, the product-contact surface of the cannula comprises or consists of fused silica (e.g., quartz silica and polyimide coating) (Polymicro, Phoenix, Ariz.). The use of fused silica for the product contact surfaces greatly reduces losses of product when compared with prior art cannulas, in which product is exposed to stainless steel. Indeed, while only 59±14% of an adeno-associated virus vector was recovered from a prior art injection device that had been pre-flushed with product, 101±6% was recovered from a device comprising a cannula of the present invention even without pre-flushing. See, Example 2.

One of skill in the art would realize that materials other than fused silica may be used in cannulas of the present invention, provided that such materials have the property of low surface-related losses of the biologically active agent in question. Tubing made of other materials may be used in place of the fused silica tubing, or alternatively the lumen of the cannula can be coated with a substance to achieve substantially the same result. The optimal material to be used may vary depending on the nature of the biologically active agent, and may be determined by experimentation.

The use of tubing with small internal diameter (ID), such as fused silica tubing with an ID of 100 μm, might be expected to reduce, rather than increase, recovery of sample due to the increased surface area to volume ratio. Perhaps surprisingly, use of small ID fused silica tubing does not cause large losses of delivered products, for example, AAV vectors. Without intending to be limited by theory, the result may be explained by the increased linear flow rate that results when a given delivery rate (volume of product delivered per unit time) is maintained constant using smaller ID tubing. In addition, AAV appears to have little affinity for the surface of the fused silica tubing, which may account for of the low losses.

The small ID of the fused silica tubing used in Example 1 has the additional advantage of reducing the hold-up volume of the system. For example, a four-foot-long segment of fused silica tubing with an ID of 100 μm has a lumen volume of less than 15 μl. Such low volumes reduce sample consumption and significantly reduce waste of sample due to the hold-up volume of the delivery system. Reduced wastage of product is particularly valuable when the biologically active agent is difficult and/or expensive to obtain, for example many recombinant proteins or gene therapy vectors.

FIG. 4 depicts an overview of an exemplary syringe pump that may be used in combination with cannulas as described herein. Shown in FIG. 4 are syringe saddle 60, syringe clamp 62, syringe clamp groove (retainer) 64, clutch lever 66, syringe driver 68, syringe plunger retainer 70, liquid crystal display 72 and on/off switch 74. Syringe pumps useful in systems with the cannulas described herein are commercially available, for example under the name Medfusion 2010i (Medex, Inc., Carlsbad, Calif.).

Figure 5:
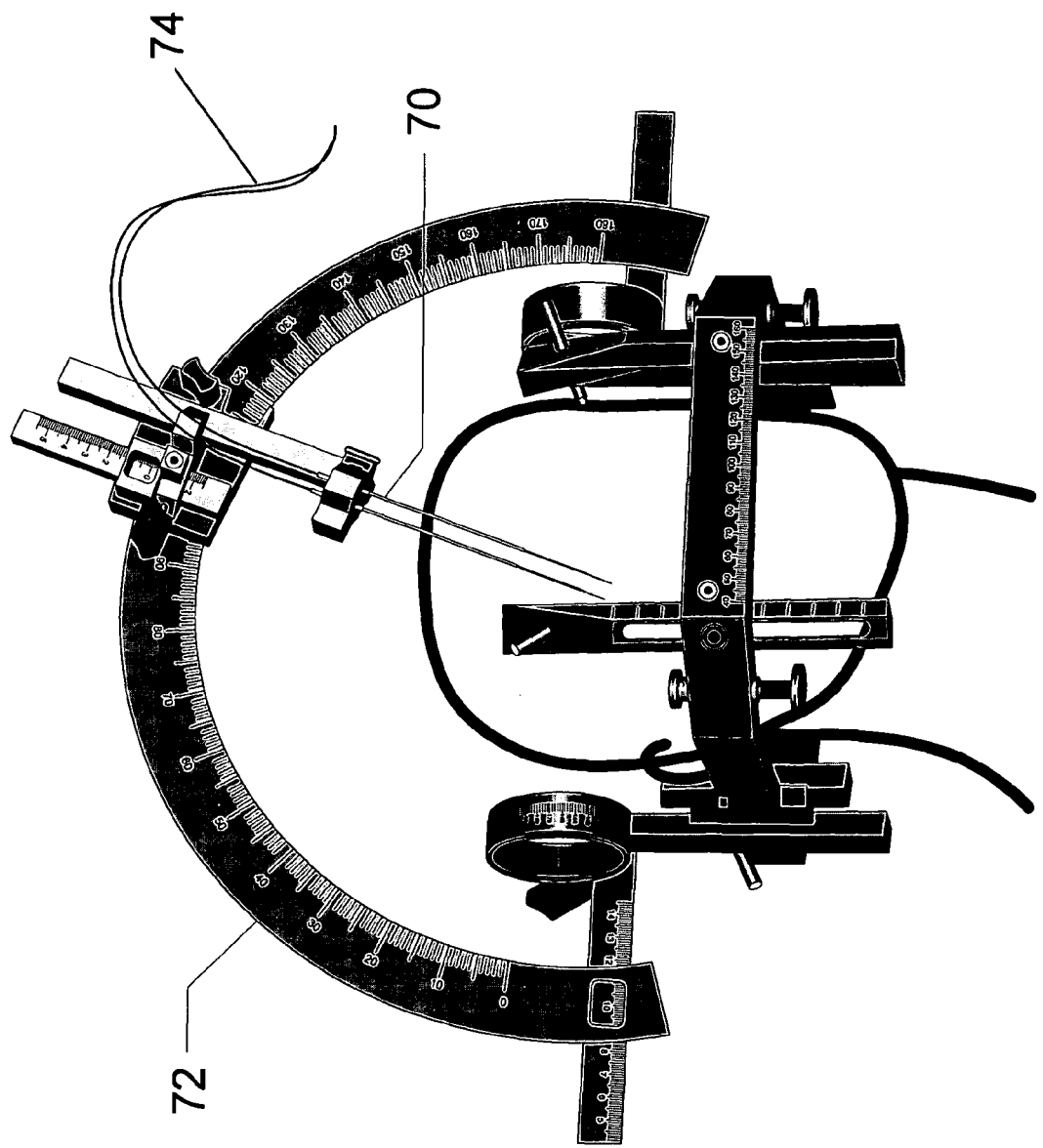

FIG. 5 depicts an overview of a system including a cannula 70 as described herein attached to a stereotactic frame 72. Cannula 70 may also be attached to syringe pump, for example via tubing 74. Stereotactic frames are commercially available, for example Lexell stereotactic frames (Ranfac Corp., Avon, Mass.).

In any of the systems described herein, the product contact portion may comprise quartz silica (fused silica tubing in the cannula), USP class VII polypropylene (syringe and Luer hubs), cyanoacrylate (glue joints), and stainless steel (23G spacer).

Typically, the systems described herein are able to deliver product to the brain with far less exposure to stainless steel than using previously described systems, in which product is in contact with stainless steel along some or all of the entire length of the cannula. Reduced exposure of product to stainless steel, as provided in the devices and systems of the present invention, reduces losses. For example, the cannula illustrated in FIG. 3B-6, as configured in the system illustrated in FIG. 1, has product contact surfaces comprising almost exclusively fused silica tubing and a USP Class VII polypropylene syringe. The only other contact surface is the glue joint between the proximal end of the fused silica tubing and the Luer hub of the syringe, at which location product contacts cyanoacrylate adhesive and the cross-sectional surface of the proximal end of the stainless steel spacer. The exposure to steel in this system is minimal.

Cannulas of the present invention may also combine the step design and the internal fused silica product contact surfaces to provide an improved cannula with reduced reflux, reduced surface-related losses of agent and reduced hold-up volume.

Cannulas of the present invention may be sterilized using techniques known in the art including, for example, by standard ethylene oxide. Sterilized cannulas may optionally be individually packaged in a Tyvek® pouch.

Agents that can be delivered using a cannula of the present invention include any material that may have a desired effect in the target tissue. For example, therapeutic drugs, proteins, plasmids or gene therapy vectors may be delivered into the brain of a subject. Non-therapeutic agents may also be added such as dyes, tracers, contrast agents and markers for imaging, diagnostic or research purposes.

For example, retroviral gene therapy systems have been described. See, e.g., U.S. Pat. No. 5,219,740; Miller and Rosman, *BioTechniques* (1989) 7:980-990; Miller, A. D., *Human Gene Therapy* (1990) 1:5-14; Scarpa et al., *Virology* (1991) 180:849-852; Burns et al., *Proc. Natl. Acad. Sci. USA* (1993) 90:8033-8037; and Boris-Lawrie and Temin, *Cur. Opin. Genet. Develop.* (1993) 3:102-109. A number of adenovirus vectors have also been described. See, e.g., U.S. Pat. Nos. 6,048,551, 6,306,652, Parks, R. J., Clin. Genet. (2000) 58:1-11; Tsai et al., Curr. Opin. Mol. Ther. (2000) 2:515-523.

Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., *Molec. Cell. Biol.* (1988) 8:3988-3996; Vincent et al., *Vaccines* 90 (1990) (Cold Spring Harbor Laboratory Press); Carter, B. J. *Current Opinion in Biotechnology* (1992) 3:533-539; Muzyczka, N. *Current Topics in Microbiol. and Immunol.* (1992) 158:97-129; Kotin, R. M. *Human Gene Therapy* (1994) 5:793-801; Shelling and Smith, *Gene Therapy* (1994) 1:165-169; and Zhou et al., *J. Exp. Med.* (1994) 179:1867-1875.

Cannulas of the present invention can be used as part of a convection-enhanced delivery (CED) system for administration to the CNS. For example, U.S. Pat. No. 6,309,634, the disclosure of which is hereby incorporated by reference in its entirety, describes methods of gene therapy in which agents are delivered to regions of the central nervous system by CED. Using CED, recombinant vectors can be delivered to many cells over large areas of the CNS. Moreover, the delivered vectors efficiently express transgenes in CNS cells (e.g., glial cells). Cannulas of the present invention may be used with any convection-enhanced delivery device for delivery of recombinant vectors. In one embodiment, the device is an osmotic pump or an infusion pump. Both osmotic and infusion pumps are commercially available from a variety of suppliers, for example Alzet Corporation (Cupertino, Calif.), Hamilton Corporation, or Alza, Inc. (Palo Alto, Calif.).

Cannulas of the present invention can also be used for direct injection or other methods of infusion, rather than CED.

Product may be delivered to a target tissue at a variety of flow rates, including but not limited to 0.2, 0.5, 0.7, 1.0, 1.5, 2.0, 3.0, 5.0, 10, 15 or 20 μl/min. With reference to the embodiments illustrated in FIGS. 1A and 2A, flow rates above 10-20 μl/min are difficult to achieve using four feet of fused silica tubing with 100 μm ID because of excessive back-pressure at such high flow rates. This does not represent a serious limitation for convection enhanced delivery methods, however, which are preferably performed at relatively low flow rates. Flow rates lower than 0.2 μl/min may be difficult to achieve using the system illustrated in FIGS. 1A and 2A because the pump lacks a slow enough setting, but one of skill in the art would be able to use a different pump and/or syringe configuration to achieve such low delivery rates.

The flow rate, and thus the pressure of the product as it is delivered to the target tissue, may be increased, decreased, or held steady throughout delivery. In a preferred embodiment, the flow rate is held substantially constant throughout delivery, rather than being "ramped up" to a plateau.

Typically, a recombinant vector is delivered via CED devices as follows. An improved cannula of the present invention is inserted into CNS tissue in the chosen subject. Stereotactic maps and positioning devices are available, for example from ASI Instruments, Warren, Mich. Positioning may also be conducted by using anatomical maps obtained by CT and/or MRI imaging to help guide the injection device to the chosen target.

Examples 2-5 disclose use of a cannula of the present invention to deliver the gene encoding hAADC to the brain of humans, rats and non-human primates. Delivery of the hAADC gene may be helpful in treatment of Parkinson's disease (PD). PD is characterized in part by the progressive loss of dopaminergic neurons in the substantia nigra and a severe decrease of dopamine in the putamen (Hornykiewicz (1975) *Nat'l Inst. Drug Abuse Res. Monogr. Ser.* (3): 13-21). AADC is an enzyme in the dopamine biosynthetic pathway that converts L-dopa to dopamine. Previous studies have shown that transfer of the cDNA encoding human AADC to rat or non-human primate putamen can reduce effective L-dopa doses in animal models of PD, and thereby restore striatal dopamine to normal levels (Bankiewicz et al. (2000) *Exp. Neurol.* 164(1): 2-14; Sanchez-Pernaute et al. (2001) *Mol. Ther.* 4(4): 324-30). In human PD patients, this therapy would be expected to lower L-dopa requirements and extend the duration during which clinical benefit of the drug is observed.

Example 2, along with associated tables and figures, provides a protocol and experimental results for delivery of a gene to the brain of a primate using a cannula of the present invention (Clinical Device B). rAAV virions encoding hAADC (AAV-hAADC-2) are infused into the putamen of four normal rhesus monkeys and the distribution of AADC expression is determined by immunohistochemistry. Two infusion protocols are tested: a ramped procedure (slow stepwise increases in rate from 0.2 µL/min to 1 µL/min), and a non-ramped infusion at a constant rate of 1 µL/min. The primary endpoints are safety evaluation of the infusion procedures and assessment of transgene expression at 5.5 weeks post-infusion.

Clinical observations after vector infusions reveal no behavioral abnormalities during the study period. No differences in gross pathology with either the ramped or non-ramped infusion procedure are observed. Histopathology is comparable in both groups, and reveals only minimal localized inflammatory tissue reaction along the needle track in response to cannula placement and vector infusion. In addition, AADC immunohistochemistry demonstrates that vector is distributed throughout the putamen, with no significant difference in volume of immunostaining with either infusion procedure. Serum antibody levels against AAV2 vector exhibited a minor increase after infusion.

The following examples are provided simply to illustrate a embodiments of the present invention, and not to define or limit the invention.

Example 1

Assembly and Packaging Procedures

A. Exemplary Cannula #1

An exemplary stepped cannula (such as shown in FIGS. 3A and 3B) was produced as follows.

Stainless steel tubing segments were cut in lengths and welded using a Lasag Nd:YAG or Neodinium YAG (Yttrium aluminum garnet) laser, an ultraviolet laser in the 454 nm wavelength region. The weld between the 23G and the 19G segments was tested to be leak free and all weld joints were tested to withstand a minimum pull force of 10 lbs. The weld between the 23G and 19G segments should be leak free to prevent any product that may reflux up the outside of the needle from leaking into the lumen of the cannula. For the same reason, the glue joint between the exposed distal end of the fused silica tubing and the steel tubing portions of the cannula should be liquid-tight.

The needle was passivated and ultrasonically cleaned after laser steps are completed. The fused silica tubing is cut and assembled to the stainless cannula with cyanoacrylate glue. A BD needle hub is attached to the distal end of the tubing to finish the assembly. Prior to packaging, a plastic needle guard is placed over the proximal end of the cannula to protect the tip, then the entire assembly is packaged in a pre-labeled Tyvek® pouch for sterilization.

The injection needle sub-assembly (INSA) was assembled by sliding a succession segments of stainless steel tubing over a core segment 20 of tubing (9.67 inches long, 23 RW cutoff, 0.0250/0.0255 OD, 0.0125/0.0140 ID, 0.006 wall). FIG. 3A. All dimensions relating to inner diameter (ID), outer diameter (OD) and tubing wall thickness ("wall") are provided in inches, with paired values X/Y representing minimum and maximum tolerances.

Referring now to FIG. 3A, segment 22 (8.28 inches long, 19 RW cutoff, 0.0415/0.0425 OD, 0.0255/0.0285 ID, 0.0075 wall) was placed over the core segment 20 to leave a 0.390 inch (10 mm) of the core extending beyond the distal end of segment 22. Segment 24 (6.31 inches long, 17 RW cutoff, 0.0575/0.0585 OD, 0.0405/0.0435 ID, 0.008 wall) was placed over the segments 20 and 22 to leave 1.970 inches of segment 22 extending beyond the distal end of segment 24. Segment 26 (6.31 inches long, 15 RW cutoff, 0.0715/0.0725 OD, 0.0595/0.0615 ID, 0.006 wall) was placed over the segments 20, 22, 24 to leave 1.970 inches of segment 22 extending beyond the distal end of segment 26. Segment 28 (6.31 inches long, 0.086/0.087 OD, 0.0735/0.0750 ID, 0.006 wall) was placed over the segments 20, 22, 24, 26 to leave 1.970 inches of segment 22 extending beyond the distal end of segment 28. Segment 30 (1.58 inches long, 0.108/0.110 OD, 0.0880/0.0895 ID, 0.010 wall) was placed over the segments 20, 22, 24, 26, 28 to leave 7.090 inches of segment 20 extending beyond the distal end of segment 30.

All components were laser welded in place. The distal weld seam between segments 20 and 22 was made 100% air tight, and the interior of segment 1 was tested to ensure that there was no blockage (e.g. using a 0.012 inch diameter wire or gage pin). All weld joints must withstand a minimum pull force of 10 pounds.

Once assembled, the INSA was passivated and ultrasonically cleaned as follows: Oakite aluminum cleaned for 10 minutes, spray rinsed with deionized water for 7 minutes, ultrasonically rinsed in alcohol, and air dried.

A needle guard 32 (9.0 inches long, 0.156 OD, 0.104/0.108 ID, 0.025 wall) is placed over assembled segments 20, 22, 24, 26, 28, 30 to leave a 0.8 inch segment of segment 30 extending beyond the proximal end of the assembled segments.

INSAs were inspected to be free of traces of acid and cleaning solution as follows: removed needle guard 32, soaked in alcohol bath, replaced needle guard 32, blew air through distal end of needle guard 7, inspected liquid effluent at proximal end of segment 20, repeated until all effluent appeared to be clean.

The distal end of the INSA was inspected to ensure that it was straight.

FIG. 3B illustrates the assembly of an exemplary injection needle assembly as described herein. As shown in FIG. 3B-1, the needle guard 32 was removed from the INSA 35 as described above, and a length of fused silica tubing 40 was threaded through the core 23G tubing of the INSA 35, starting at the proximal end, until approximately 2 inches extended beyond the distal end of the INSA 35. Loctite® adhesive (Loctite® Prism® 4011 adhesive, low viscosity) was applied to the exposed fused silica tubing 40, and then the fused silica tubing was withdrawn until approximately 1 inch remained beyond the distal end of the INSA while spinning the INSA to evenly distribute adhesive. The bond strength of the adhesive bond is at least 5 pounds. The exposed fused silica tubing is trimmed so that 0.390 inches (10 mm) remained extending from the distal end of the INSA, and the needle guard 32 was replaced.

A 48 inch length of FEP (Teflon) tubing (1/16 OD, 0.030 ID) was prepared 31 and both ends were dipped in Loctite® primer (Loctite® 7701 primer) and air dried. The proximal end of the fused silica tubing 40 was threaded through the FEP tubing. Loctite® adhesive was applied to the proximal end of the INSA. The distal end of the FEP tubing 31 was quickly pushed over the needle end of the INSA. The bond strength of the adhesive bond is at least 4 pounds.

As shown in FIG. 3B-3, a 23G stainless steel spacer 47 (1 inch long, 23 RW) was placed over the fused silica tubing 40. Loctite® adhesive was applied to the outside of the fused silica tubing 40 and to the outside of the spacer 47, and the spacer 47 was inserted into the proximal end of the FEP tubing 31 until the proximal ends were flush. A 0.5 inch long segment of PVC shrink tubing 49 (0.125 ID) was slipped over the proximal end of the FEP tubing 31.

As depicted in FIG. 3B-4, a 1/16 female Luer compression fitting 50 was then slipped over the proximal end of the FEP tubing 31 and a ferrule 51 was placed approximately 1 inch over the proximal end of the FEP tubing 31. Loctite® adhesive is applied to the outside of the FEP tubing 31 and the ferrule 51 was pushed to place the proximal end of the ferrule flush with the proximal end of the FEP tubing 31. Loctite® adhesive is applied to seal the joints between the fused silica tubing 40, spacer 47, FEP tubing 31 and the ferrule 51.

The remaining fused silica tubing 40 extending proximally beyond the ferrule 51 was scored and snapped off. As shown in FIG. 3B-5, the ferrule 51 was then seated snuggly in the Luer compression fitting 50 (3 pound minimum pull force) and the heat shrink tubing 49 was then heat shrinked over the joint between the proximal end of the INSA 35 and the FEP tubing 31.

The assembly was tested for air leaking, and a male Luer cap 55 was added to the compression fitting 50. (FIG. 3B-6).

The assembled INA may then be packaged and sealed in a Tyvek® pouch (4×23 inches) with a label, and placed in a labeled box for storage or shipment.

Although the tubing 31 was made of Teflon FEP, one of skill in the art would recognized that any suitable tubing material could be used, or the tubing could be omitted altogether. The FEP tubing 31 was included as protection for the fused silica tubing 40, and to help make sure the very thin fused silica tubing was visible to operators of the system. Neither of these functions is essential. In addition, because the FEP tubing does not contact product tubing of other materials may be used without regard to biocompatibility.

The finished cannula produced as described in herein comprises five layers of stainless steel tubing over 6.31 inches of its length (e.g. the length comprising tubing element 28), with an internal diameter of 0.0125-0.0140 inches and an exterior diameter of 0.086 to 0.087 inches. This cannula has substantial rigidity along this segment, which prevents flexing of the cannula as it is inserted into the target tissue (e.g. the brain). In addition, a sixth layer of steel tubing 30 adds even greater strength to the cannula over a 1.58 inch segment, which prevents the cannula from being crushed or deformed when it is mounted in a stereotactic frame during use, as illustrated in FIG. 5.

B. Exemplary Cannula #2

Figure 6:
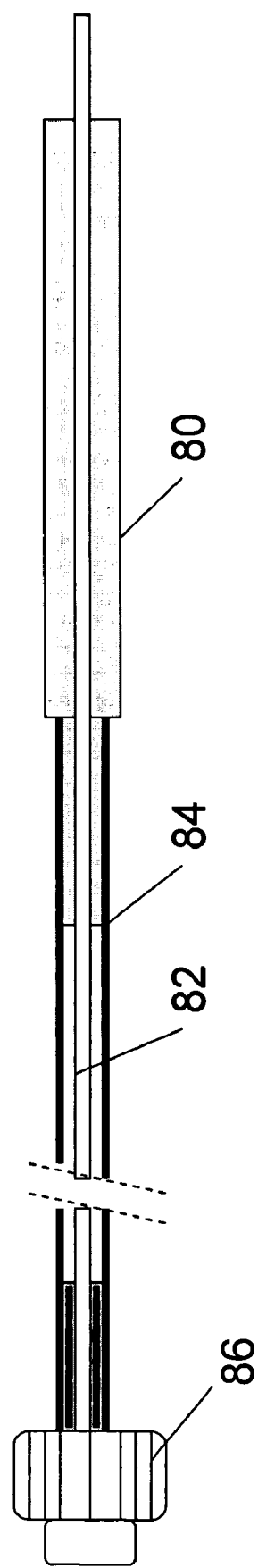

Another cannula was produced similar to the one described in Example 1A. As shown in FIG. 6, the cannula 80 is composed of four layers of 304 surgical steel fused together by laser welding in a step design, ending in 30 gauge tubing. The steel cannula (approximately 24.6 cm from end to end, including needle tip) is lined with fused silica of 100 μm inner diameter 82 which also forms the tip of the delivery device by extending 1 cm beyond the steel. Approximately 1.2 meters (122 cm) of additional fused silica 82 covered with Teflon tubing 84 connect to a Luer hub 86. A 1-inch 30 gauge steel spacer 88 between the fused silica and Teflon tubing is sealed and attached to the Luer hub with medical grade cyanoacrylate glue.

Example 2

Delivery of Recombinant Viral Vectors Encoding AADC to Primate Brain

Recombinant AAV vector encoding human AADC (AAV-hAADC-2) was prepared and delivered to the putamen of rhesus monkeys as follows.

Recombinant Vector Production

Recombinant AAV2 was generated by a triple transfection protocol (Matsushita et al. (1998) *Gene Ther.* 5(7): 938-45). Briefly, after expansion of cells from the HEK 293 working cell bank through a series of disposable culture ware in DMEM containing 10% fetal bovine serum and 2 mM glutamine, cells were co-transfected with three plasmids (pAAV-hAADC-2, pHLP 19 and pladeno5). The rAAV-hAADC-2 vector clone is the same as that described previously (Sanftner et al. (2004) *Mol. Ther.* 9(3): 403-9). Plasmids pHLP 19 and pladeno5 are described more fully at U.S. Pat. Nos. 5,139,941; 5,622,856; 6,001,650 and 6,004,797, the disclosures of which are hereby incorporated by reference in their entireties.

After an appropriate transfection time, the medium containing the transfection reagent was replaced with serum-free medium and the cells were incubated further to allow vector production. Cells were harvested, concentrated by centrifugation, and lysed by a freeze/thaw method to release the AAV-hAADC-2 vector. After centrifugation to remove cellular debris, the lysate was treated with Benzonase®, calcium chloride, and precipitated with polyethylene glycol. Vector was purified by two cycles of isopycnic gradient ultracentrifugation in cesium chloride. AAV-hAADC-2 was concentrated, and diafiltered with sterile, buffered saline (PBS) containing 5% sorbitol. Poloxamer 188™ (0.001%) was added, the material is sterile filtered (0.22 μm), and stored frozen at −70° C. Vector purity was assessed by SDS-PAGE. Purified rAAV2 vector used in this study showed only VP1, VP2, and VP3 by silver staining of SDS-PAGE gels. Titer was determined by real-time Q-PCR analysis of vector genomes.

Surgical Procedures

Magnetic resonance imaging (MRI) was performed on each monkey prior to surgery to identify stereotaxic coordinates (based on the anatomical structure of the putamen). Two sites were targeted in each hemisphere with one site centered in the rostral putamen and a second in the caudal putamen. Adult rhesus monkeys (n=4) were immobilized with a mixture of ketamine (Ketaset®, 10 mg/kg, intramuscular injection) and Valium® (0.5 mg/kg, intravenous injection), intubated and prepared for surgery. Isotonic fluids were delivered intravenously at 2 mL/kg/hr. Anesthesia was induced with isoflurane (Aerane®, Omeda PPD, Inc., Liberty, N.J.) at 5% v/v, and then maintained at 1%-3% v/v for the duration of the surgery. The animal's head was placed in an MRI-compatible stereotaxic frame. Core temperature was maintained with a circulating water blanket while electrocardiogram, heart rate, oxygen saturation and body temperature are continuously monitored during the procedure. Burr-holes were made in the skull with a dental drill to expose areas of the dura just above the target sites. AAV-hAADC-2 was infused by CED (Lieberman et al. (1995) *J. Neurosurg.* 82(6): 1021-9; Bankiewicz et al. (2000) *Exp. Neurol.* 164(1): 2-14). Each monkey received a total of $3 \times 10^{11}$ vg in 200 μL spread over four sites (50 μL per site with two sites per hemisphere). Infusion cannulae were manually guided to the putamen in each brain hemisphere, and the animals received bilateral infusions (i.e. sequential infusions to the rostral and caudal sites within both hemispheres) of AAV-hAADC-2 ($1.5 \times 10^{12}$ vg/mL) at infusion rates of 0.2 μL/min (10 min), 0.5 μL/min (10 min), 0.8 μL/min (10 min) and 1 μL/min (35 min) for the left hemisphere and a constant rate of 1 μL/min (50 min) for the right hemisphere. Actual stereotaxic coordinates for each animal were: MR15101M rostral putamen AP: 18, ML: ±10.5, DV:20, caudal putamen AP: 15, ML: ±13, DV: 20, R21101M rostral putamen AP:24, ML: ±12.5, DV: 20, caudal putamen AP:21, ML: ±13.5, DV:20, MR15109M rostral putamen AP: 12, ML: ±13, DV:20, caudal putamen AP: 15, ML: ±12, DV: 20, R23700M rostral putamen AP: 21, ML: ±13.5, DV:21, caudal putamen AP: 24, ML: ±12.5, DV: 20. Approximately 10 minutes after infusion, the cannulae were removed, the wound sites were closed, and the monkey was monitored for recovery from anesthesia and then returned to its home cage for continuing observations.

Histology and Immunohistochemistry

For histological studies, animals were perfused via intracardiac saline infusion followed by 10% neutral buffered formalin (NBF). The brains were then removed and sliced in a brain mold into coronal blocks (8-10 mm). Harvested brain blocks were fixed by immersion in 10% NBF fixative. The tissue blocks were transferred 2-3 days after fixation into ascending concentrations of PBS/sucrose solution (10, 20 and 30%) over a 3-5 day period. Brains were frozen in a bath of isopentane, cooled on dry ice and cut serially into 40 μm thick coronal sections on a cryostat. Every tenth section was stained with Hematoxylin and Eosin (H&E) solutions (Richard Allen Scientific, Kalamazoo, Mich.) for histopathological analysis. Immunohistochemistry was carried out on freefloating sections with a primary antibody specific for AADC (Chemicon, Temecula, Calif., 1:1,500). Sections were incubated in 3% hydrogen peroxide for 30 min to quench endogenous peroxidases. After blocking for non-specific binding with 10% normal goat serum, sections were incubated in primary antibody overnight at room temperature, then with a biotinylated anti-rabbit IgG antibody (Vector Laboratories, Burlingame, Calif., 1:300) with streptavidin-conjugated horseradish peroxidase (Vector Laboratories, 1:300) at room temperature, both for 1 h. The complex was visualized with 3-3'-diaminobenzidine (DAB, Vector Laboratories) and hydrogen peroxide. Sections were mounted on Superfrost Plus® slides (Brain Research Laboratories, Newton, Mass.), dried, dehydrated in ascending ethanol series, cleared in xylene, and mounted with Cytoseal-XYL (Richard-Allen Scientific, Kalamazoo, Mich.). Anterior-to-posterior distribution of hAADC immunostaining was determined by the formula (n×10×40 μm) where n is the number of sections with hAADC-positive cells, 40 μm is the thickness of the section, and every tenth section was examined. The volume of distribution was estimated in serial sections (every tenth), stained for AADC with the Optical Fractionator-Optical Dissector design-based stereology method under 63× magnification on a Zeiss microscope equipped with a video camera and Stereoinvestigator™ stereology software (Microbrightfield, Williston, Vt.). CEE is <5% for each group. Results are reported as mean±SD. Student's t-test was used to measure statistical significance.

Real-Time Quantitative PCR

The vector AAV-hAADC-2 used in this study contains the human AADC target cDNA. The real-time Q-PCR primers and probe anneal to exons 2 and 3 of the AADC gene, spanning an intron not present in the vector sequence, thereby minimizing amplification of genomic DNA. Real-time Q-PCR is standardized with linearized plasmid DNA containing the vector insert and vector genomes were quantified as described previously (Sommer et al. (2003) *Mol. Ther.* 7(1): 122-8).

Neutralizing AAV Antibody Titering

The neutralizing antibody (NAb) titer of serum or plasma was determined in vitro in a cell-based assay. A defined number of AAV2 vector particles encoding a β-galactosidase reporter gene (AAV2-LacZ) were incubated with test serum for 1 h at 37° C. before addition of the mixture to HEK-293 cells near confluence in 96-well plates. Control (100%) AAV2 transduction was defined as the amount of β-galactosidase activity measured in culture 24 h after transduction with AAV2-LacZ in the presence of naïve mouse serum (NMS). A half-log serial dilution of the test serum in NMS was made to determine the highest dilution of test serum that results in 50% or greater inhibition of β-galactosidase expression. Each dilution series was tested in triplicate. A reference plasma with a well-defined AAV2 neutralizing titer was run in each assay and a negative control (NMS only) was used to determine the assay background. The titer of NAb was defined as the two dilutions that bracket the 50% inhibition level, e.g. 1:100 to 1:316.

Bridging ELISA

Titer plates (96 well) were coated with AAV2 particles and then incubated with test sample (serum or plasma). Plates were rinsed and then incubated with biotinylated AAV2 particles, which were then detected with HRP-conjugated Streptavidin. The biotinylated AAV2 particles can only be captured by multivalent antibodies forming a bridge between two AAV2 particles. A very low non-specific background signal in this assay permitted testing of undiluted or low dilutions of test articles, and the assay has higher sensitivity than a classical ELISA, in which primary antibody in the test sample is detected by an enzyme-conjugated secondary antibody. The bridging assay allows direct titer comparisons between different species and classes of antibodies. The assay was standardized with known amounts of purified mouse monoclonal antibody "A20" that recognizes AAV2 (Grimm et al. 1998). The quantification limit of this assay was approximately 15 ng/mL anti-AAV2 antibody. Human samples with a NAb titer of 1:100 contained between 1 and 10 μg/mL of antibody equivalent to A20. The average inter-assay variability for 65 human samples that underwent replicate testing by this assay was 23%.

Experimental Design

Recombinant AAV2 vectors transduce brain tissue efficiently, but transduction levels decline significantly in the presence of high neutralizing antibodies (NAb) titers (>1: 1200) (Sanftner et al. (2004) *Mol. Ther.* 9(3): 403-9). Therefore, four male rhesus monkeys with NAb titers of ≦1:100 were selected for AAV2 infusions (Table 1). MRI scans were performed prior to AAV2 delivery to determine stereotaxic coordinates for vector administration. Animals were bilaterally infused with $1.5 \times 10^{11}$ vg of AAV-hAADC-2 in two 50 μL infusions ($7.5 \times 10^{10}$ vg/site) in each hemisphere ($3.0 \times 10^{11}$ vg/brain). Ascending infusion rates (ramp) of 0.2 μL/min (10 min), 0.5 μL/min (10 min.), 0.8 μL/min (10 min) and 1 μL/min (35 min) were used for the left hemispheres, whereas a constant rate of 1 μL/min for 50 min (non-ramp) was used for the right hemispheres. Animals were monitored for 5.5 weeks, a time span satisfactory for hAADC expression to become relatively stable. Primary endpoints included AADC expression as determined by immunohistochemistry and safety assessments as determined by clinical observations and histopathology. In addition, serum samples, collected at baseline and at the end of the study, were tested for the presence of both neutralizing and total antibodies against AAV.

TABLE 1

ANTI-AAV SERUM ANTIBODY (NAB) TITERS AND BRIDGING ELISA DATA

| Non-human Primate ID | Sample | NAb Titer | Bridging ELISA (μg/mL anti-AAV Ab) |
|---|---|---|---|
| MR15102M | Pre-treatment | 1:1-1:3.1<br>1:3.1-1:10 | 0.036 |
| | Post-treatment | 1:1-1:3.1<br>1:3.1-1:10 | 0.24 ± 0.08 |
| MR15109M | Pre-treatment | 1:3.1-1:10<br>1:3.1-1:10 | Below Detection (<0.015) |
| | Post-treatment | 1:3.1-1:10<br>1:3.1-1:10 | 0.43 ± 0.35 |
| R211101M | Pre-treatment | 1:1-1:3.1<br>1:1-1:3.1 | 0.11 |
| | Post-treatment | 1:31-1:100<br>1:10-1:31 | 0.63 ± 0.07 |
| R23700M | Pre-treatment | 1:10-1:31<br>1:31-1:100 | 0.24 |
| | Post-treatment | 1:31-1:100<br>1:100-1:316 | 1.3 ± 0.7 |

Infusion Device Development and Vector Recovery

A prototype infusion device for human use ("Clinical Device A," or CDA) was composed of a 25-cm stainless steel cannula, made to fit a standard Leksell® stereotaxic frame. The CDA cannula was composed of four stepped layers of medical grade stainless steel tubing to provide rigidity and minimize internal hold-up volume. The steel CDA cannula was connected to a syringe via 1.2 meters of Teflon® tubing. Vector recovery studies at flow rates up to 1 μL/min reveal that 90% of the vector product was adsorbing to the device (Table 2), despite the 0.01% Poloxamer 188 included as a surfactant in the product formulation. A 1-hr flush of the device with vector improves subsequent recovery, but vector loss was still approximately 40%. Further testing for vector absorption included testing of stepped stainless steel cannulas in which the product contacts different tubing materials at flow rates of ≦1 μL/min. (Example 1A and 1B). Excellent vector recovery was observed for cannulas comprising fused silica, Tygon®, and silicone tubing in contact with the AAV vector. Other materials such as steel, Teflon (PTFE and FEP) and polyimide bound significant amounts of vector.

TABLE 2

VECTOR RECOVERY: PRECLINICAL, CLINICAL DEVICE A AND CLINICAL DEVICE B

| | Preclinical Device | Clinical Device A | Clinical Device B |
|---|---|---|---|
| Product contact surfaces | Fused silica, Teflon ®, polypropylene (Luer couplings) | No. 304 stainless steel, Teflon ®, polypropylene (Luer lock and syringe) | Fused silica, polypropylene (Luer and syringe) |
| Internal hold-up volume | variable | 350 μL | 12 μL |
| Vector recovery after ≦50 μL flush volume (±SD) | 63 ± 16% | 9 ± 4% | 101 ± 6% |
| Vector recovery after 500 μL of flush at 8 μl/min (±SD) | not done | 60 ± 15% | not done |

Much of the vector loss was observed only at low flow rates. For example, in Teflon tubing, vector loss was inversely proportional to the linear flow rate. Ninety percent of the vector was lost at 1 μl/min (4 mm/min through 1.2 meters of tubing), whereas acceptable vector recovery (>80%) could be attained in the same tubing at flow rates above 100 μL/min. In order to maximize the linear flow rate and to eliminate all contact of vector with Teflon and steel surfaces, the entire core of the clinical device was lined with fused silica of inner diameter 100 μm (Example 1B, FIG. 6). In this device ("Clinical Device B", or CDB), the steel cannula surrounds the fused silica to provide rigidity, and the fused silica extends 10 mm beyond the tip of the steel cannula (FIG. 6). Two external steps near the needle tip are included to minimize potential reflux along the needle track. An additional 1.2 meters of fused silica connects the CDB cannula to a Luer hub and is covered by Teflon tubing only to provide protection. The CDB was manufactured and assembled in accordance with cGMP and terminally sterilized by ethylene oxide gas.

Quantitative recovery of vector was evaluated through mock infusions with preclinical and clinical devices. For the preclinical device, 400 μL of vector solution was drawn from the distal end into a length of Teflon tubing that was then coupled to a 7 cm cannula composed of fused silica surrounded by a 4 cm piece of 27-gauge steel tubing. After filling the cannula at 100 μL/min, an additional 20 μL flush was dispensed before collecting vector for recovery assays. Four samples were collected from two devices at flow rates from 0.2 to 1.0 μL/min (ramped procedure) with a programmable syringe pump.

As shown in Table 2, the average vector recovery from the preclinical devices under these conditions was 63±16% (±SD). For the clinical devices, AAV-hAADC-2 vector was diluted to $5 \times 10^{11}$ vg/mL, loaded into syringes and attached to the devices. After fill, Clinical Device A was flushed with 500 μL of vector solution at 8 μL/min (62.5 min), while Clinical Device B was flushed with a total of 50 μL of vector solution at 4 μL/min (12.5 min). Two sequential aliquots of 50 μL were collected from three sets of each device at flow rates from 0.2 to 1.0 μL/min. Vector concentration in each sample was determined by real-time quantitative PCR (Q-PCR).

Recovery for Clinical Device A was only 60±15% after the extensive one-hour flush, whereas complete recovery of vector (101±6%) was observed for Clinical Device B. Potency of vector samples recovered from Clinical Device B was confirmed by determining the infectious titer (see, Zhen et al.

(2004) *Hum. Gene Ther.* 15(7):709-715. No significant decrease in specific activity (infectious units/vg) was observed.

Immunohistochemistry and Quantitation of hAADC Expression In-Vivo

Immunohistochemical analysis of hAADC expression was performed on each brain hemisphere at 5.5 weeks post-AAV-hAADC-2 infusion to determine if the vector distribution was different after ramped vs. non-ramped infusion with Clinical Device B. All monkeys exhibited hAADC expression within the putamen. Serial sections were examined with brightfield microscopy for hAADC-positive cells. The volume of distribution and Anterior-Posterior (A-P) spread of hAADC transgene-positive cells were determined for all animals.

Figure 7:
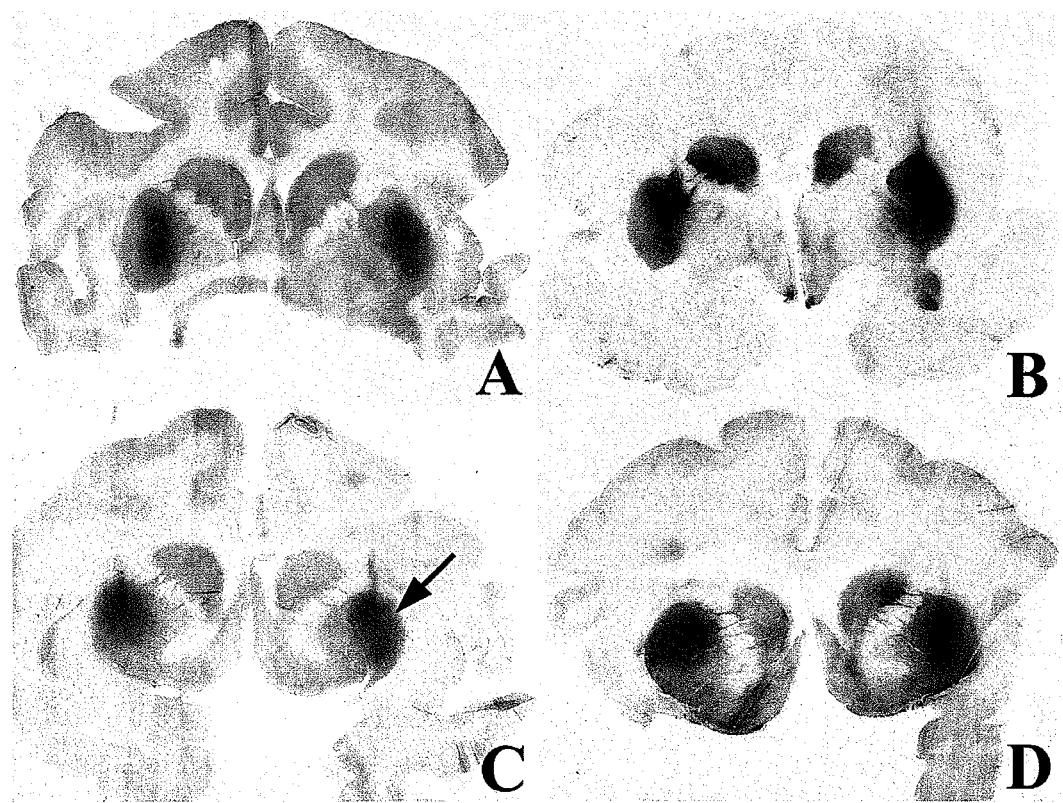
FIG. 7, panels A-D, depict results of immunohistochemical staining for aromatic L-amino acid decarboxylase (AADC) in whole mounted brain sections from monkeys used in the experiments described in Example 2. Brains are shown in coronal section through the infusion site at 5.5 weeks post-infusion. Panels A, B, C, and D represent the four different monkey brains analyzed in Example 2 [MR15102M (A), MR15109M (B), R23700M (C) and R211101M (D)]. All left hemispheres received ramped infusion and all right hemispheres received non-ramped infusion. The black arrow indicates the putamen region.

FIG. 7 shows immunohistochemical staining for the hAADC transgene in cross-sections through the infusion site. Images are of whole mounts of sections from animals MR15102M (A), MR15109M (B), R23700M (C) and R21110M (D). Sections are oriented from a caudal view with the right hemisphere on the right side of the image and the left hemisphere on the left side of the image. In all animals, transgene expression was localized to the putamen. No hAADC expression was detected in cortical regions except in direct line with the infusion track as illustrated in FIG. 7B. No difference in the number of AADC-positive cells or intensity of hAADC staining was seen in a comparison of the right and left hemispheres.

Figure 8:
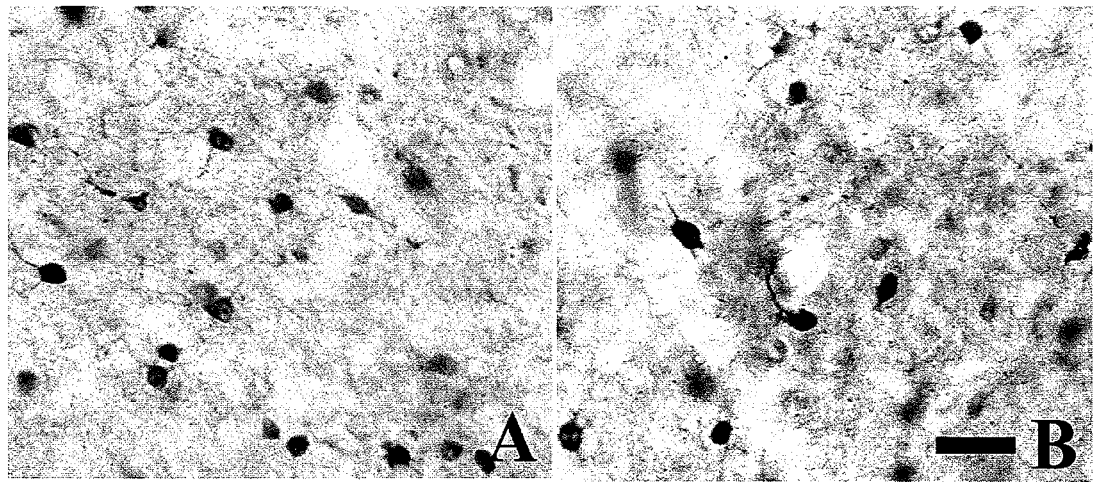
FIG. 8, panels A and B, depict high magnification images of immunohistochemical staining for AADC within the putamen of the brain of a monkey used in the experiments described in Example 2 at 5.5 weeks post-infusion. A representative section from the hemisphere that received ramped infusion is shown in FIG. 8A and one from the hemisphere that received non-ramped infusion is shown in FIG. 8B. The scale bar represents 100 µm.

A higher magnification image of the infusion site of the putamen in a representative animal from the left hemisphere that received ramped infusion (FIG. 8A), or the right hemisphere that received non-ramped infusion (FIG. 8B) illustrates the hAADC transgene expression in medium spiny neurons. Immunohistochemical staining for hAADC expression was seen in all (8/8) of the infused hemispheres. AAV-hAADC-2 administration resulted in good expression and coverage of the putamen with a similar distribution of AAV-hAADC-2 with either the ramped (left hemisphere) or non-ramped (right hemisphere) infusion procedure.

Quantitation of the estimated volume of hAADC distribution in serial sections stained with anti-hAADC antibody was performed with Stereoinvestigator™ stereology software (Microbrightfield, Williston, Vt.). The Anterior-Posterior (A-P) distribution, a one dimensional measure of distribution from rostral to caudal, and volume of hAADC immunostaining were determined separately for each hemisphere of the four AAV-treated non-human primates (Table 3). The mean A-P distribution and the mean volume for either the right or left hemisphere were each based on four hemispheres. The mean A-P distribution for the left hemisphere (ramped delivery) was 9,600 µm±2,422 µm (SD) and the mean volume was 238 mm$^3$±121 mm$^3$. The mean A-P distribution for the right hemisphere (non-ramped delivery) was 9,606 µm ±2,037 µm and the mean volume was 284 mm$^3$±55 mm$^3$. There was no significant difference in mean volume or mean A-P distribution between ramped or non-ramped by an unpaired Student's t-test (P=0.9973 for A-P distribution comparison and P=0.5187 for spread volume comparison). The non-ramped infusion did not result in reflux of vector along the cannula track or a decrease in transgene-derived hAADC distribution. The lack of reflux may also in part be due to the multiple step design of the cannula.

TABLE 3

ANTERIOR-TO-POSTERIOR (A-P) DISTANCE OF SPREAD AND SPREAD VOLUME OF AADC IN NON-HUMAN PRIMATES INFUSED WITH AAV-hAADC-2

| | A-P Distribution (µm) | Spread volume (mm$^3$) |
|---|---|---|
| Right (non-ramped infusion) Animal I.D. | | |
| MR15109 | 8,822 | 272.1 |
| R23700M | 12,400 | 346.5 |
| R211101M | 9,600 | 301.5 |
| MR15102M | 7,600 | 214.4 |
| Mean right hemisphere (non-ramped infusion) | 9,606 | 283.6 |
| Standard Deviation | 2,037 | 55.4 |
| Left (ramped infusion) Animal I.D | | |
| MR15109 | 8,400 | 110.2 |
| R23700M | 12,800 | 402.3 |
| R211101M | 10,000 | 217.3 |
| MR15102M | 7,200 | 222.2 |
| Mean left hemisphere (ramped infusion) | 9,600 | 238.0 |
| Standard Deviation | 2,422 | 121.1 |

Histopathology

Figure 9:
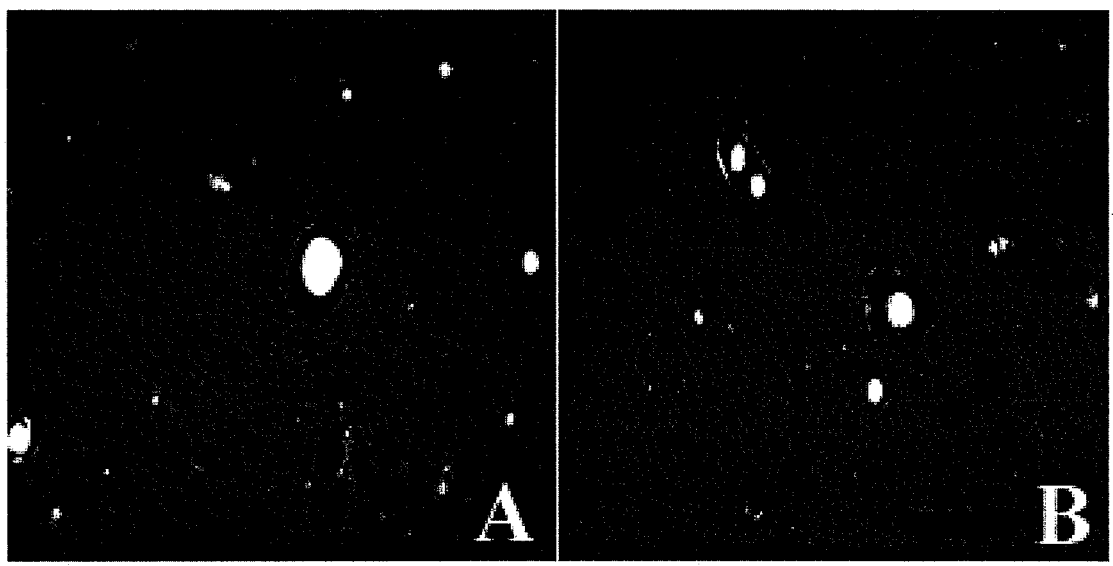
FIG. 9, panels A and B, depict Hematoxylin and Eosin (H&E) stained sections within the putamen from a representative animal used in the experiments in Example 2, R211101M, at 5× magnification. Animal R211101M received bilateral CED of AAV-hAADC-2 using the non-ramped infusion procedure in the right hemisphere (FIG. 9A) and the ramped infusion procedure in the left hemisphere (FIG. 9B). Images illustrate the area adjacent to the cannula track, and were taken at the mid-caudal putamen level. The scale bar represents 400 µm.

Histopathological analysis of serial sections stained with H&E was performed on all animals to determine the effect of cannula placement and AAV-hAADC-2 infusion with either ramped or non-ramped delivery. FIG. 9 shows H&E stained sections within the putamen from a representative animal, R211101M, at 5× magnification. Animal R211101M received bilateral CED of AAV-hAADC-2 by the non-ramped infusion procedure in the right hemisphere (Panel A) and the ramped infusion procedure in the left hemisphere (Panel B). Images illustrate the area adjacent to the cannula track at the mid-caudal putamen level. All H&E stained slides were reviewed by a neuropathologist (Pathology Associates Inc.), blinded to treatment conditions. Some mononuclear cellular infiltration was seen in the putamen with mild perivascular cuffing. Both putamina contained a few infiltrated blood vessels and mild parenchymal infiltration. Histopathologic appearance of the right and left hemispheres was similar, with slight inflammatory tissue reaction at the infusion site.

Development of Neutralizing Antibodies

Neutralizing antibody (NAb) and total antibody titers to AAV capsid were determined for serum samples collected prior to infusion of vector, and at the time of necropsy. Slight rises in anti-AAV antibody levels were detected by bridging ELISA in all animals after bilateral infusion of AAV-hAADC-2 (Table 1). The results for two NAb assays are shown in Table 1. The bridging ELISA is standardized with anti-AAV2 mouse monoclonal antibody. The average of two results is shown for post-treatment samples and a single result is shown for pre-treatment samples. The animal (R23700M) with the highest serum neutralizing antibody titer (1:10 to 1:100) before treatment has a post-treatment antibody increase to 1:31-1:316 on Day 42. This animal had similar hAADC transgene distribution when compared to the other animals and thus there was no apparent inhibition of vector spread associated with the higher titer.

Clinical Observations

Monkeys were evaluated daily for clinical signs, food consumption, and body weight. Post-surgical daily clinical observations indicated that the animals tolerated the CED procedure well and did not display behavioral changes. There were no AAV-hAADC-2 treatment-related clinical signs or changes in body weight. Observations made during the post-treatment period were similar to those commonly observed in laboratory-housed rhesus monkeys that undergo similar surgical procedures.

Results

An embodiment of the cannula of the present invention was tested to assess its ability to effectively deliver rAAV vector to primate brain, which may serve as a model for delivery of therapeutic rAAV vectors for treatment of Parkinson's disease in a human subject. Mock infusions designed to test vector delivery established that essentially 100% of the intended dose can be delivered with a cannula as described herein, preferably avoiding contact of vector with Teflon or steel surfaces.

Stereotaxic administration of AAV-hAADC-2 into the putamen of four non-human primates was performed by comparison of a ramped (graded increase in infusion rate) vs. a non-ramped (constant rate) infusion procedure. Expression of hAADC was detectable by immunohistochemistry and was distributed broadly in the putamen. Stereological quantitation of the volume of transgene-derived hAADC demonstrated similar distribution in hemispheres receiving either infusion procedure. Furthermore, the constant flow rate did not result in excessive vector deposits along the needle track. Histopathologic analysis revealed only slight tissue inflammatory reaction localized to the area of the cannula insertion track, suggesting no safety concerns. There was no apparent difference in the degree of cellular infiltration or inflammation between the left and right putamen (i.e. ramped vs. non-ramped infusion). No abnormal clinical observations were seen after surgery and intraputamenal infusion in any animals.

In addition to device and infusion parameters, another important consideration for effective AAV-mediated gene delivery into any compartment is potential neutralization by anti-AAV antibodies. There is a broad range of pre-existing AAV neutralizing antibody titers in humans (Blacklow et al. (1968) *J. Natl. Cancer Inst.* 40(2): 319-27) that have the potential of adversely affecting the efficacy of gene therapy techniques. Any AAV-mediated gene therapy approach must anticipate such hurdles.

For example, in a model system utilizing SCID mice wherein human AAV2-neutralizing antibody titers could be established at various levels, it was observed that titers <1:10 significantly impacted liver transduction of AAV-Factor IX after intravenous administration (Scallan et al. (2004) American Society of Gene Therapy, Minneapolis, Minn., Abstract # 753 S286). Delivery of AAV2 to the putamen was assumed to be less subject to neutralization by circulating antibodies due to the immune-privileged status of the CNS. In fact, studies performed in rats pre-immunized systemically with AAV2 and then infused intrastriatally confirmed significant protection from neutralization with a decrease in transduction observed only when Nab titers exceeded 1:1200 (Sanftner et al. (2004) *Mol. Ther.* 9(3): 403-9).

Experiments described herein utilized animals with pre-existing NAb titers ranging from 1:1 to 1:100 in order to exclude neutralizing antibodies as a confounding variable, and these titers have no apparent impact on hAADC expression in putamen. Moreover, post-infusion titers rose only slightly after vector administration, thereby affirming well-targeted and minimally-disruptive gene delivery with the current device and infusion conditions. These results also suggest that repeat intrastriatal infusions of AAV2 may be feasible in human patients.

In summary, non-ramped infusion of AAV-hAADC-2 to monkey putamen via an infusion device of the present invention (Clinical Device B) was well tolerated. Transgene (hAADC) expression and distribution in the putamen were comparable to more complicated and time-consuming ramp-up flow conditions. Given that gene therapy of neurodegenerative diseases and other CNS disorders is an expanding field (Tinsley and Eriksson (2004) *Acta Neurol. Scand.* 109(1): 1-8), the present results suggest that the design of Clinical Device B represents an important advancement in methodology for this field. The device and infusion parameters of the present invention are likely to be applicable for striatal delivery of AAV2 in PD patients, and also for targeting different anatomic sites, delivering a variety of therapeutic drugs or gene therapy agents, and treating an assortment of CNS clinical indications.

Examples are intended to illustrate the invention and do not by their details limit the scope of the claims of the invention. While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

All publications, patents, and patent application publications, and referred to herein are hereby incorporated by reference in there entireties.

What is claimed is:

1. A method of delivering one or more materials to the brain of a subject, the method comprising the steps of:
   a) positioning a stepped cannula in the brain of the subject, wherein the stepped cannula reduces reflux of the one or more materials in the brain of the subject and wherein the stepped cannula comprises:
      i. two or more co-axially disposed segments, each segment having an exterior diameter that defines the exterior diameter of the cannula, wherein the exterior diameter of the segments is different; and
      ii. one or more tubular components extending through the lumen of the cannula, wherein at least one tubular component comprises a tubing that reduces loss of material delivered to the brain through the cannula, and further wherein the at least one tubular component extends from 1 mm to 10 mm beyond the distal end of the lumen;
   b) delivering the one or more materials to the brain through the cannula using a convection enhanced delivery pump, wherein at least one material comprises an adeno-associated virus (AAV) vector.

2. The method of claim 1, wherein the at least one tubular component extends from 1 mm to 5 mm beyond the distal end of the lumen.

3. The method of claim 1, wherein the cannula comprises two, three, four, five or six co-axially disposed segments.

4. The method of claim 1, wherein the exterior diameter of the segments decreases from the proximal end to the distal end of the cannula.

5. The method of claim 1, wherein the cannula has a constant interior diameter.

6. The method of claim 1, wherein the cannula comprises five stainless steel segments.

7. The method of claim 1, wherein the tubing that reduces loss of material is a fused silica tubing.

8. The method of claim 7, wherein the cannula further comprises FEP tubing disposed around the fused silica tubing.

9. The method of claim 1, wherein the two or more co-axially disposed segments comprise stainless steel.

10. The method of claim 9, wherein the lumen of one or more of the stainless steel segments is coated with one or more polymers.

11. The method of claim 1, wherein the lumen of the cannula is operably connected to a reservoir comprising the one or more materials to be delivered through the cannula.

12. The method of claim 11, wherein the reservoir is operably linked to the one or more tubing components extending through the lumen of the cannula.

13. The method of claim 11, wherein the reservoir comprises a syringe.

14. The method of claim 13, wherein the syringe is operably linked to the pump.

15. The method of claim 14, wherein the pump is programmable.

16. A system for delivering one or more materials to the brain of a subject, said system comprising:
   a) the one or more materials, wherein at least one material comprises an adeno associated virus vector;
   b) a stepped cannula for delivering the one or more materials, wherein the stepped cannula reduces reflux of the one or more materials in the brain of said subject and wherein the cannula comprises:
      i. two or more co-axially disposed segments, each segment having an exterior diameter that defines the exterior diameter of the cannula, wherein the exterior diameter of the segments is different; and
      ii. one or more tubular components extending through the lumen of the cannula, wherein at least one tubular component comprises a tubing that reduces loss of material delivered to the brain through the cannula, and further wherein the at least one tubular component extends from 1 mm to 10 mm beyond the distal end of the lumen; and
   c) a convection enhanced delivery pump operably linked to the stepped cannula.

17. The system of claim 16, wherein the at least one tubular component extends from 1 mm to 5 mm beyond the distal end of the lumen.

18. The system of claim 16, wherein the cannula comprises two, three, four, five or six co-axially disposed segments.

19. The system of claim 16, wherein the exterior diameter of the segments decreases from the proximal end to the distal end of the cannula.

20. The system of claim 16, wherein the cannula has a constant interior diameter.

21. The system of claim 16, wherein the cannula comprises five stainless steel segments.

22. The system of claim 16, wherein the tubing that reduces loss of material is a fused silica tubing.

23. The system of claim 22, wherein the cannula further comprises FEP tubing disposed around the fused silica tubing.

24. The system of claim 16, wherein the two or more co-axially disposed segments comprise stainless steel.

25. The system of claim 24, wherein the lumen of one or more of the stainless steel segments is coated with one or more polymers.

26. The system of claim 16, wherein the lumen of the cannula is operably connected to a reservoir comprising the one or more materials to be delivered through the cannula.

27. The system of claim 26, wherein the reservoir is operably linked to the one or more tubing components extending through the lumen of the cannula.

28. The system of claim 26, wherein the reservoir comprises a syringe.

29. The system of claim 28, wherein the syringe is operably linked to the pump.

30. The system of claim 29, wherein the pump is programmable.

* * * * *